United States Patent
Razmara et al.

(10) Patent No.: US 12,171,525 B2
(45) Date of Patent: Dec. 24, 2024

(54) UNMANNED MOBILE ROBOT AND SOFTWARE FOR CLINICAL EXAMINATION AND TREATMENT

(71) Applicant: METAOPTIMA TECHNOLOGY INC., Vancouver (CA)

(72) Inventors: Majid Razmara, Vancouver (CA); Maryam Sadeghi, Vancouver (CA); Hessam Maleki, Burnaby (CA); Margaret Stella Atkins, Vancouver (CA)

(73) Assignee: MetaOptima Technology Inc., Vancouver (CA)

( * ) Notice: Subject to any disclaimer, the term of this patent is extended or adjusted under 35 U.S.C. 154(b) by 648 days.

(21) Appl. No.: 17/432,876

(22) PCT Filed: Feb. 24, 2020

(86) PCT No.: PCT/CA2020/050234
§ 371 (c)(1),
(2) Date: Aug. 20, 2021

(87) PCT Pub. No.: WO2020/176969
PCT Pub. Date: Sep. 10, 2020

(65) Prior Publication Data
US 2022/0202294 A1 Jun. 30, 2022

Related U.S. Application Data

(60) Provisional application No. 62/814,175, filed on Mar. 5, 2019.

(51) Int. Cl.
*A61B 5/00* (2006.01)
*A61N 5/06* (2006.01)
(Continued)

(52) U.S. Cl.
CPC ............ *A61B 5/0077* (2013.01); *A61B 5/444* (2013.01); *A61B 5/445* (2013.01); *A61B 5/4842* (2013.01);
(Continued)

(58) Field of Classification Search
None
See application file for complete search history.

(56) References Cited

U.S. PATENT DOCUMENTS

| | | |
|---|---|---|
| 6,711,293 B1 | 3/2004 | Lowe |
| 9,573,684 B2 | 2/2017 | Kimchi et al. |

(Continued)

FOREIGN PATENT DOCUMENTS

| | | |
|---|---|---|
| CN | 108566513 A | 9/2018 |
| EP | 1504713 A1 | 2/2005 |

(Continued)

OTHER PUBLICATIONS

Webpage https://www.youtube.com/watch?app=desktop&v=mtTiPnNUKj8&embeds_referring_euri=https%3A%2F%2Fforbot.pl%2F&feature=emb_imp_woyt (Year: 2015).*

(Continued)

*Primary Examiner* — James M McPherson
(74) *Attorney, Agent, or Firm* — Oyen Wiggs Green & Mutala LLP

(57) ABSTRACT

A method for photographing at least a portion of a subject is disclosed, the method comprising: generating a photography scheme, the photography scheme comprising a set of photography control points, each of the photography control points comprising: a location of the platform relative to the subject; an orientation of the platform relative to the subject; and one or more photography parameters; determining a location and an orientation of the platform carrying the imaging system; navigating the platform to each of the (Continued)

photography control points and operating the imaging system to capture an image of the subject at each of the photography control points according to the associated photography parameters. A method of administering photodynamic therapy to a subject is also disclosed.

15 Claims, 23 Drawing Sheets

(51) Int. Cl.
G01S 15/93 (2020.01)
G05D 1/689 (2024.01)
B64U 10/14 (2023.01)
B64U 30/20 (2023.01)
B64U 101/30 (2023.01)
G03B 15/00 (2021.01)
G03B 17/56 (2021.01)
G03B 35/02 (2021.01)

(52) U.S. Cl.
CPC .............. *A61N 5/062* (2013.01); *G01S 15/93* (2013.01); *G05D 1/689* (2024.01); *A61B 2562/04* (2013.01); *A61N 2005/0626* (2013.01); *A61N 2005/0642* (2013.01); *A61N 2005/0661* (2013.01); *B64U 10/14* (2023.01); *B64U 30/20* (2023.01); *B64U 2101/30* (2023.01); *G03B 15/006* (2013.01); *G03B 17/561* (2013.01); *G03B 35/02* (2013.01)

(56) References Cited

U.S. PATENT DOCUMENTS

| 10,378,906 | B2 | 8/2019 | O'Brien et al. | |
|---|---|---|---|---|
| 11,340,618 | B2* | 5/2022 | Lacaze | G05D 1/0214 |
| 2008/0033410 | A1 | 2/2008 | Rastegar et al. | |
| 2017/0296099 | A1* | 10/2017 | Hancock | A61B 5/11 |
| 2017/0301109 | A1 | 10/2017 | Chan et al. | |
| 2018/0002010 | A1* | 1/2018 | Bauer | B64C 39/024 |
| 2018/0003656 | A1* | 1/2018 | Michini | G01N 25/72 |
| 2018/0004207 | A1* | 1/2018 | Michini | G01S 1/024 |
| 2018/0095478 | A1* | 4/2018 | van Cruyningen | G01S 19/14 |
| 2018/0255465 | A1* | 9/2018 | Priest | H04W 16/18 |
| 2018/0259652 | A1* | 9/2018 | Shimizu | G06T 7/70 |
| 2018/0319497 | A1* | 11/2018 | Priest | B60L 53/80 |
| 2020/0207474 | A1* | 7/2020 | Foggia | B64C 27/08 |
| 2020/0361338 | A1* | 11/2020 | James | B64C 39/024 |
| 2024/0069547 | A1* | 2/2024 | Martirosyan | G06T 7/292 |

FOREIGN PATENT DOCUMENTS

| EP | 3330823 A1 | 6/2018 |
|---|---|---|
| WO | 2011004358 A1 | 1/2011 |
| WO | 2017020856 A1 | 2/2017 |
| WO | 2018089268 A1 | 5/2018 |
| WO | 2019076759 A1 | 4/2019 |

OTHER PUBLICATIONS

Amer, K. et al., "Deep Convolutional Neural Network-Based Autonomous Drone Navigation", 2019.
Vu, H. et al., "High Accuracy and Visibility-Consistent Dense Multiview Stereo", IEEE Transactions on Pattern Analysis and Machine Intelligence, vol. 34, No. 5, May 2012.
Alcantarilla, P. et al., "Fast Explicit Diffusion for Accelerated Features in Nonlinear Scale Spaces", Proceedings British Machine Vision Conference 2013, pp. 13.1-13.11.
Barnes, C. et al., "PatchMatch: A Randomized Correspondence Algorithm for Structural Image Editing", ACM Transactions on Graphics (Proc. SIGGRAPH), 28(3), Aug. 2009.
Moulon, P. et al., "Adaptive Structure from Motion with a contrario model estimation", ACCV 2012.
https://www.fotofinder-systems.com/, retrieved Jun. 17, 2019.
https://www.canfieldsci.com/imaging-systems/vectra-xt-3d-imaging-system/, retrieved Jun. 17, 2019.
https://www.canfieldsci.com/imaging-systems/vectra-m3-3d-imaging-system/, retrieved Jun. 17, 2019.
DermoScan X2 printout, retrieved Jun. 17, 2019.
Calonder, M. et al., "BRIEF: Computing a local binary descriptor very fast", IEEE Trans. Pattern Anal. Machine Intell.,34(7), 1281-1298, 2011.
Bircher, A. et al., "Structural Inspection Path Planning via Iterative Viewpoint Resampling with Application to Aerial Robotics", 2015 IEEE International Conference on Robotics and Automation, May 1, 2015, pp. 6423-6430.

* cited by examiner

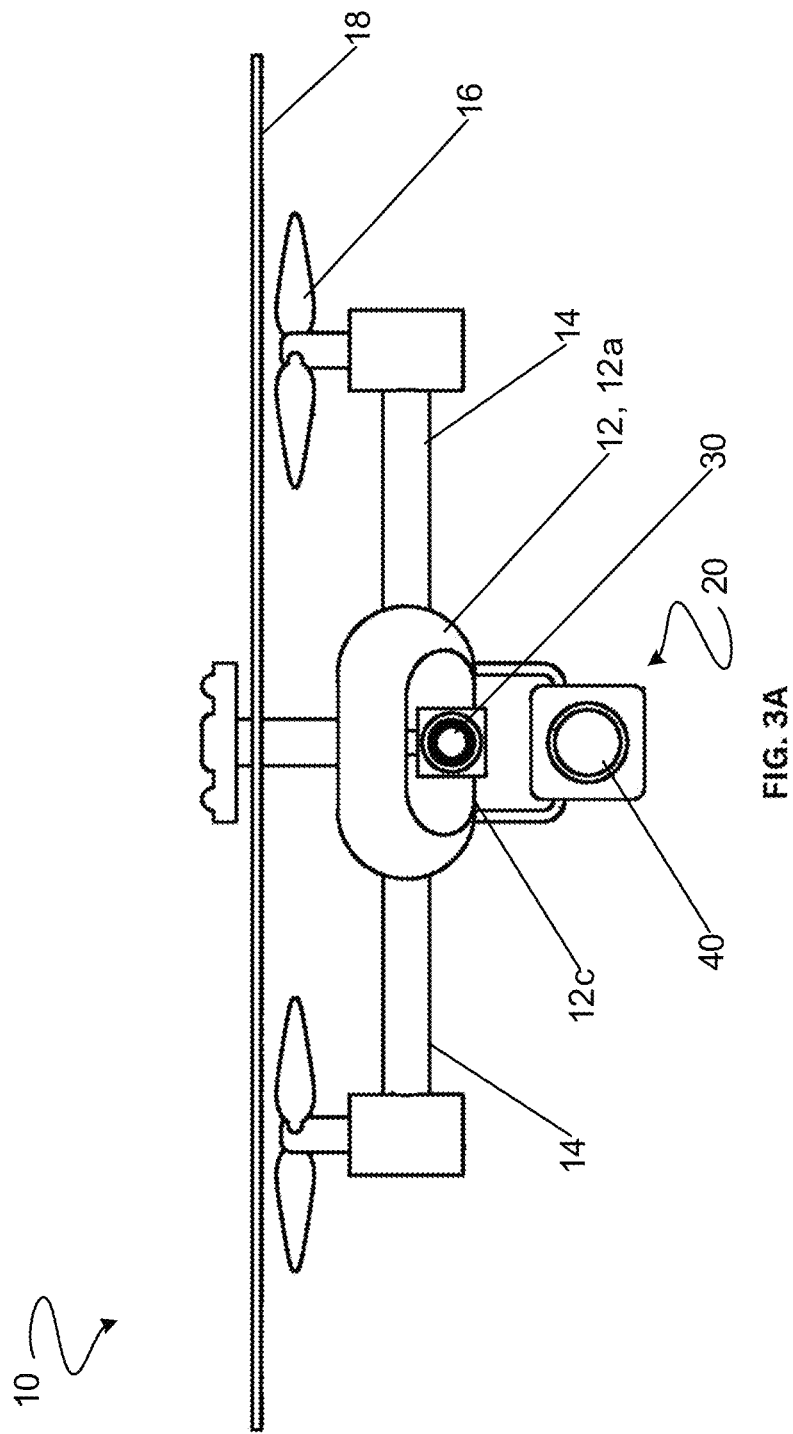

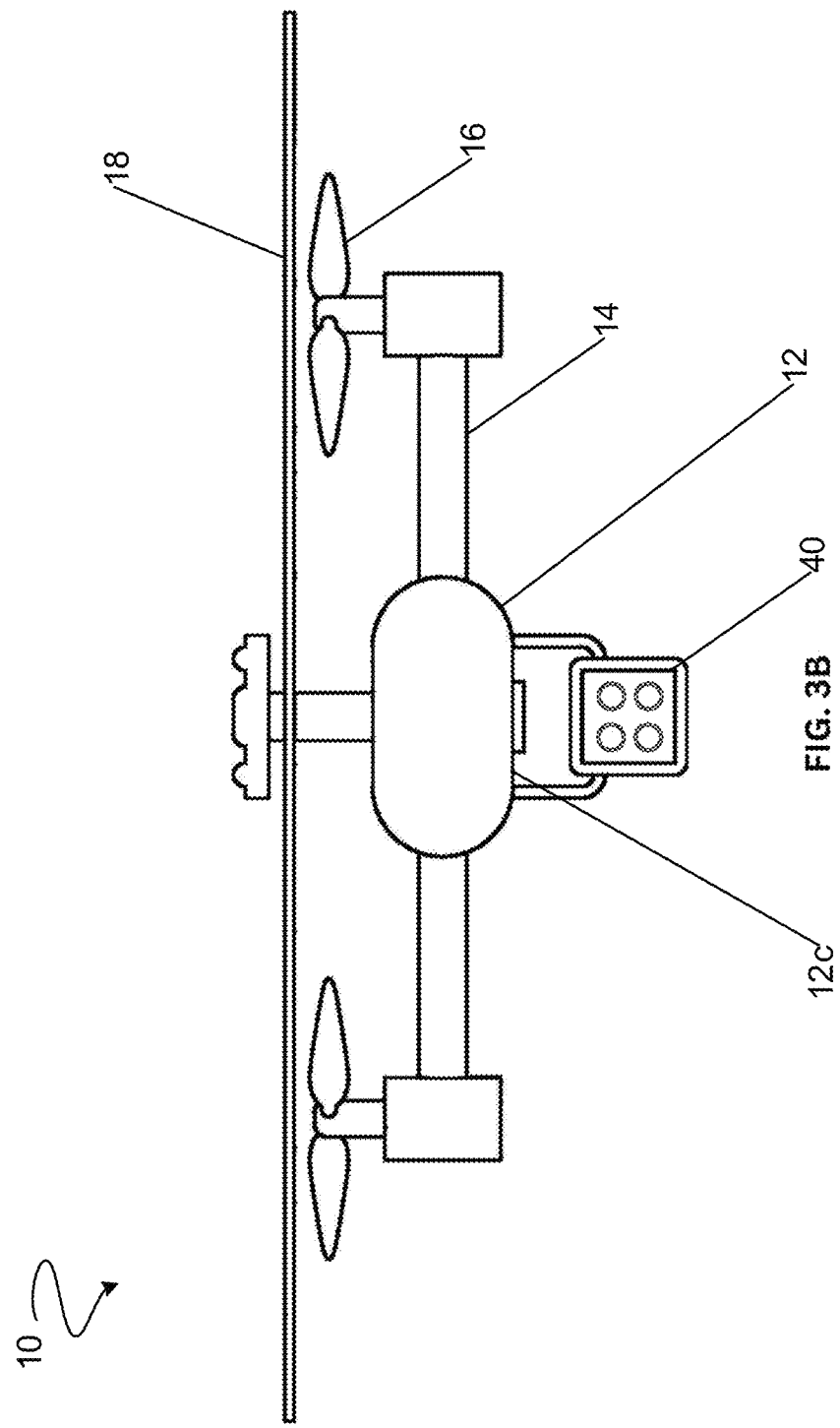

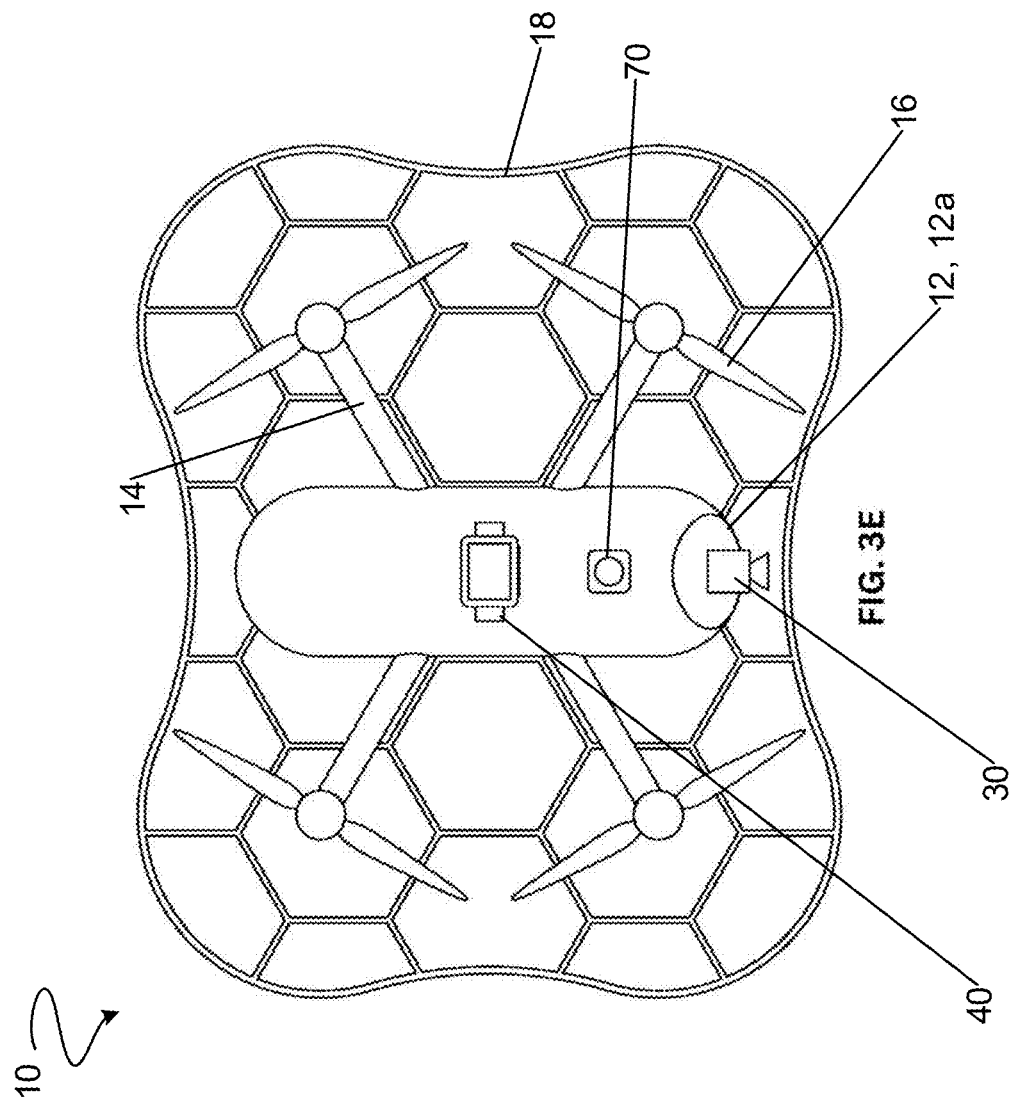

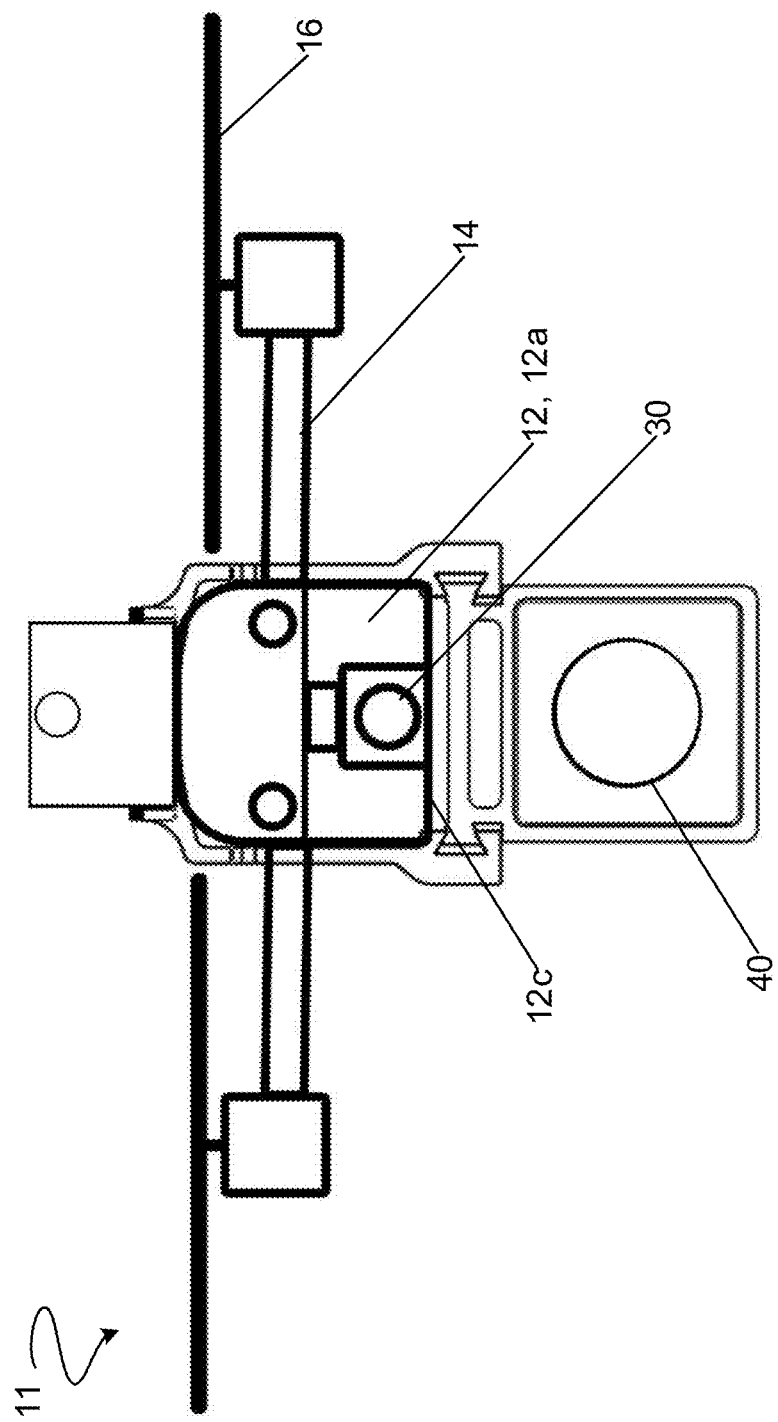

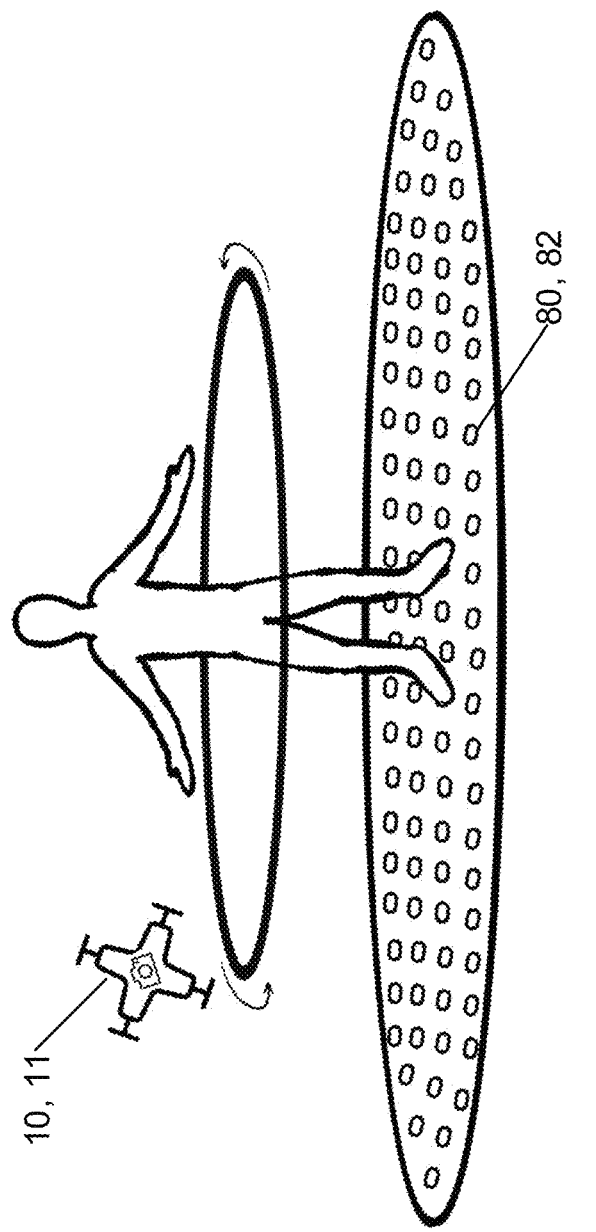

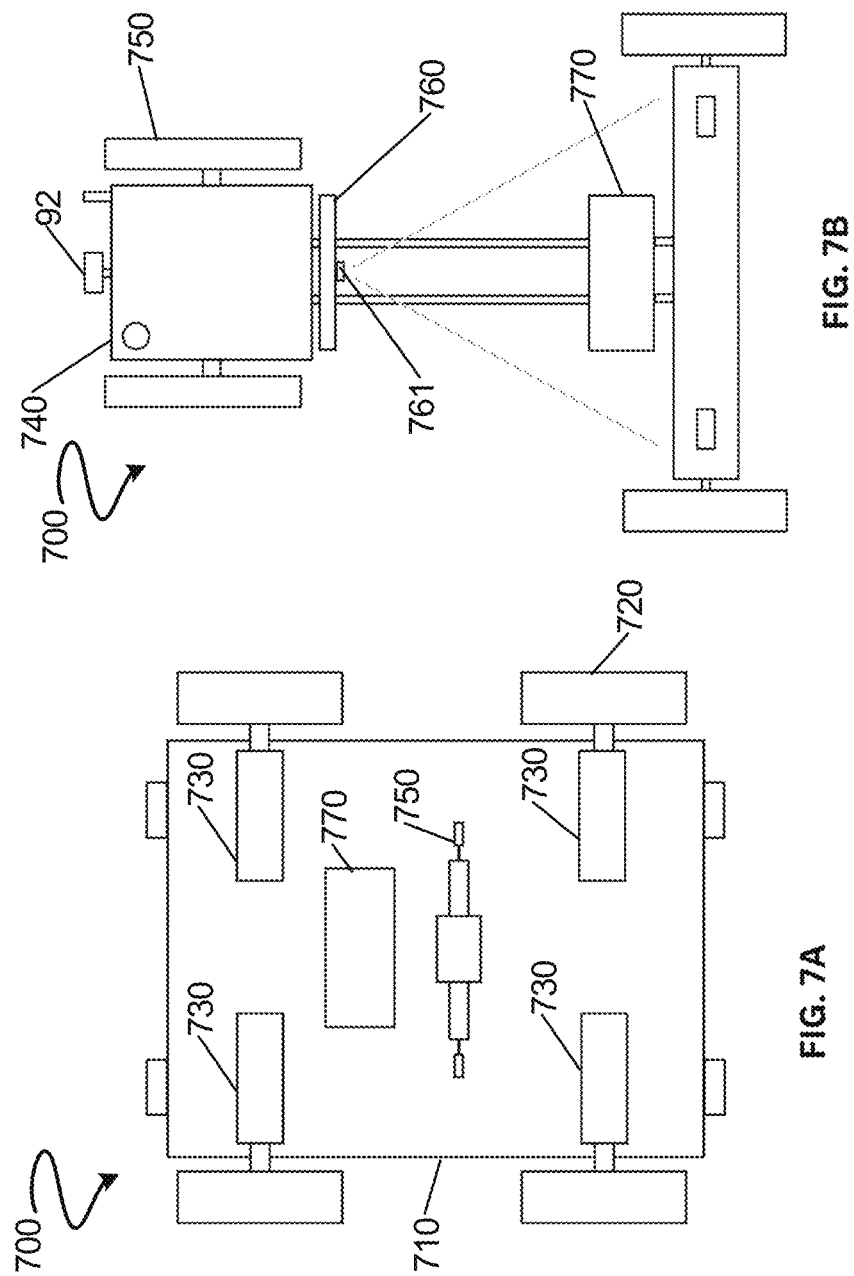

UNMANNED MOBILE ROBOT AND SOFTWARE FOR CLINICAL EXAMINATION AND TREATMENT

REFERENCE TO RELATED APPLICATIONS

This application claims priority from U.S. Patent Application Ser. No. 62/814,175, entitled DRONE AND SOFTWARE FOR IMAGING SKIN, filed Mar. 5, 2019 which is hereby incorporated herein by this reference in its entirety for all purposes. For purposes of the United States of America this application claims the benefit of U.S. Patent Application Ser. No. 62/814,175, entitled DRONE AND SOFTWARE FOR SKIN IMAGING, filed Mar. 5, 2019.

TECHNICAL FIELD

This application relates to systems and methods for imaging and/or treating the surface of a subject, for example a subject's skin. Example embodiments provide systems and methods for imaging and treating using a self-propelled apparatus, for example an unmanned aerial vehicle (UAV).

BACKGROUND

There are many applications that require imaging a subject. For example, many medical examinations require imaging a patient's body or a portion thereof. Medical applications of body imaging include diagnosis and monitoring of conditions afflicting a patient's skin, eyes, mouth, or nails. Furthermore, many of these afflictions require monitoring over a period of time to diagnose and treat.

One condition benefiting from monitoring over time is skin cancer. Furthermore, early diagnosis of skin cancer may improve patient outcome. Skin screening is one method to achieve early diagnosis of skin cancer. Performed regularly, self-examination can alert an individual to changes in the skin and aid in the early detection of skin conditions and diseases. However, naked eye examination lacks the sensitivity required for early-stage detection of some skin conditions and diseases, for example skin cancer. Furthermore, differences in imaging conditions, for example differences in lighting between different imaging sessions, may limit the utility of such monitoring.

To diagnose and treat conditions and diseases, dermatologists and other health professionals may systemically check the entire surface of the skin, hair, and nails, and especially areas exposed to the sun. Skin lesions (e.g. parts of the skin that have abnormal appearance compared to the skin around them) and hair and nail features may be recorded by hand by plotting a full-body chart or by taking a series of images.

Total body photography (TBP) is the process of imaging skin, hair, and nails to detect, monitor, diagnose, and treat conditions and diseases. TBP may be used to measure other metrics, including, but not limited to body shape for cosmetic and/or fitness and/or health applications.

Manually capturing images is both resource intensive and is susceptible to errors. Images must be properly documented and analyzed to optimize diagnosis and treatment. Incongruities in, for example, lighting, the angle that the image is acquired at, etc. may impact the quality of images and affect detection and diagnosis.

TBP systems are known. Some systems employ numerous cameras positioned to surround a patient and simultaneously capture images. Other systems employ multiple cameras positioned to simultaneously capture images of a section of a patient's body. Such conventional systems are typically bulky, expensive, and require a dedicated space and personnel to operate. Further, depending on the position and angle of the cameras relative to the patient's body, the quality of the acquired images may be affected, thereby complicating detection and diagnosis. Further still, since a patient's body dimensions change and the patient's positioning relative to the cameras is difficult to replicate over time, it is difficult to reproduce the multiple variables that impact the acquisition of consistent images (e.g. the position of the patient's body or body segment relative to the camera, the distance of the patient's body or segment from the camera, the orientation of the camera, lighting, etc.). Thus, it is difficult to reproduce high quality and consistent images of skin, hair, and nail segments that are needed to monitor skin, hair, and nail features over time.

Skin conditions may be treated with photodynamic therapy, wherein a lesion is illuminated with light of a certain intensity for a period of time. Treating skin conditions with photodynamic therapy poses similar difficulties to imaging of skin. In particular, it is difficult to accurately administer photodynamic therapy, and consistently administer photodynamic therapy during multiple treatment sessions.

There is a general desire for an imaging and/or treatment system capable of producing high quality, reproducible images, and/or administering photodynamic therapy.

The foregoing examples of the related art and limitations related thereto are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

One aspect of the invention provides a method of photographing at least a portion of a subject with a platform carrying an imaging system, the method comprising: generating a photography scheme, the photography scheme comprising a set of photography control points, each of the photography control points comprising: a location of the platform relative to the subject; an orientation of the platform relative to the subject; and one or more photography parameters; determining a location and an orientation of the platform carrying the imaging system; navigating the platform to each of the photography control points and operating the imaging system to capture an image of the subject at each of the photography control points according to the associated photography parameters.

One aspect of the invention provides an imaging system comprising: an unmanned aerial drone, the drone comprising: a drone body; four rotors mounted to the drone body; a digital camera mounted to the drone body; a light source mounted to the drone body; a laser sensor mounted to the drone body; a drone transceiver mounted to the drone body; a drone computer mounted to the drone body, the drone computer configured to: control the four rotors to navigate the drone; control the digital camera to capture one or more digital images; control the light source to emit light; receive data from the laser sensor; and transmit and receive data via the drone transceiver; three GPS receivers, wherein each of the GPS receivers is configured to receive a signal from the drone transceiver; a controller, the controller comprising: a memory storing at least one previous image of a subject; a controller transceiver configured to communicate with the drone transceiver and the three GPS receivers; wherein the controller is configured to control the drone to: control the rotors to navigate the drone about a subject; control the rotors to orientate the digital camera towards the subject; control the light source to illuminate the subject; control the digital camera to take one or more images of the subject; and store the one or more images of the subject in the memory.

One aspect of the invention provides a method of administering photodynamic therapy to a subject with a platform carrying a photodynamic treatment system, the method comprising: receiving a photodynamic therapy prescription, the photodynamic therapy prescription comprising: a therapy region corresponding to an area of the subject; and a therapy light dose; generating a photodynamic therapy scheme at least in part based on the photodynamic therapy prescription; wherein the photodynamic therapy scheme comprises a set of photodynamic control points, each of the photodynamic control points comprising: a location of the platform relative to the subject; an orientation of the platform relative to the subject; an illumination intensity; and an illumination time; and navigating the platform to each of the photodynamic control points and controlling the photodynamic treatment system to illuminate the subject with light of the illumination intensity and for the illumination time of each of the photodynamic control points.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

FIGS. 3A to 3E depict an unmanned aerial drone (UAV) according to an example embodiment.

FIGS. 4A to 4D depict a UAV according to another example embodiment.

FIGS. 5A to 5C depict a localization system according to an example embodiment.

FIGS. 7A and 7B depict an unmanned ground vehicle (UGV) according to an example embodiment.

DESCRIPTION

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

Unless the context dictates otherwise, the term "optical element" (as used herein) refers to a lens, a filter, an optical film, a diffuser, or a polarizer.

Unless the context dictates otherwise, the term "diffuser" (as used herein) refers to a filter that diffuses or scatters light in some manner. A diffuser may be applied to provide soft light and/or to achieve a more uniform light distribution.

Unless the context dictates otherwise, the term "polarizer" (as used herein) refers to an optical filter that can convert a beam of light of undefined or mixed polarization into a beam of well-defined polarization.

Unless the context dictates otherwise, the term "linear polarizer" (as used herein) refers to a polarizer that selectively passes or creates a linearly-polarized electromagnetic wave (e.g. a linearly-polarized light wave). The direction of the electric field of the electromagnetic wave is aligned parallel to a polarization direction or 'polarization axis' of the polarizer.

Unless the context dictates otherwise, the term "circular polarizer" (as used herein) refers to a polarizer filter that selectively passes and/or creates a circularly-polarized electromagnetic wave. In a circularly-polarized wave a direction of the electric component of the electromagnetic wave changes in a rotary manner along the direction of propagation. Circular polarization can be either clockwise or counterclockwise.

Unless the context dictates otherwise, the term "cross polarization" refers to the polarization of light in an orthogonal direction to the polarization of light being discussed.

Unless the context dictates otherwise, "focal length" (as used herein) refers to the distance between a lens and a focal point of an optical system, wherein the lens converges parallel rays of light into the optical system's focal point. The focal length of an optical system is a measure of how strongly the system converges or diverges light. A system with a shorter focal length has greater optical power than one with a longer focal length since the system with the shorter focal length is able to bring light rays into focus in a shorter distance.

Figure 1A:
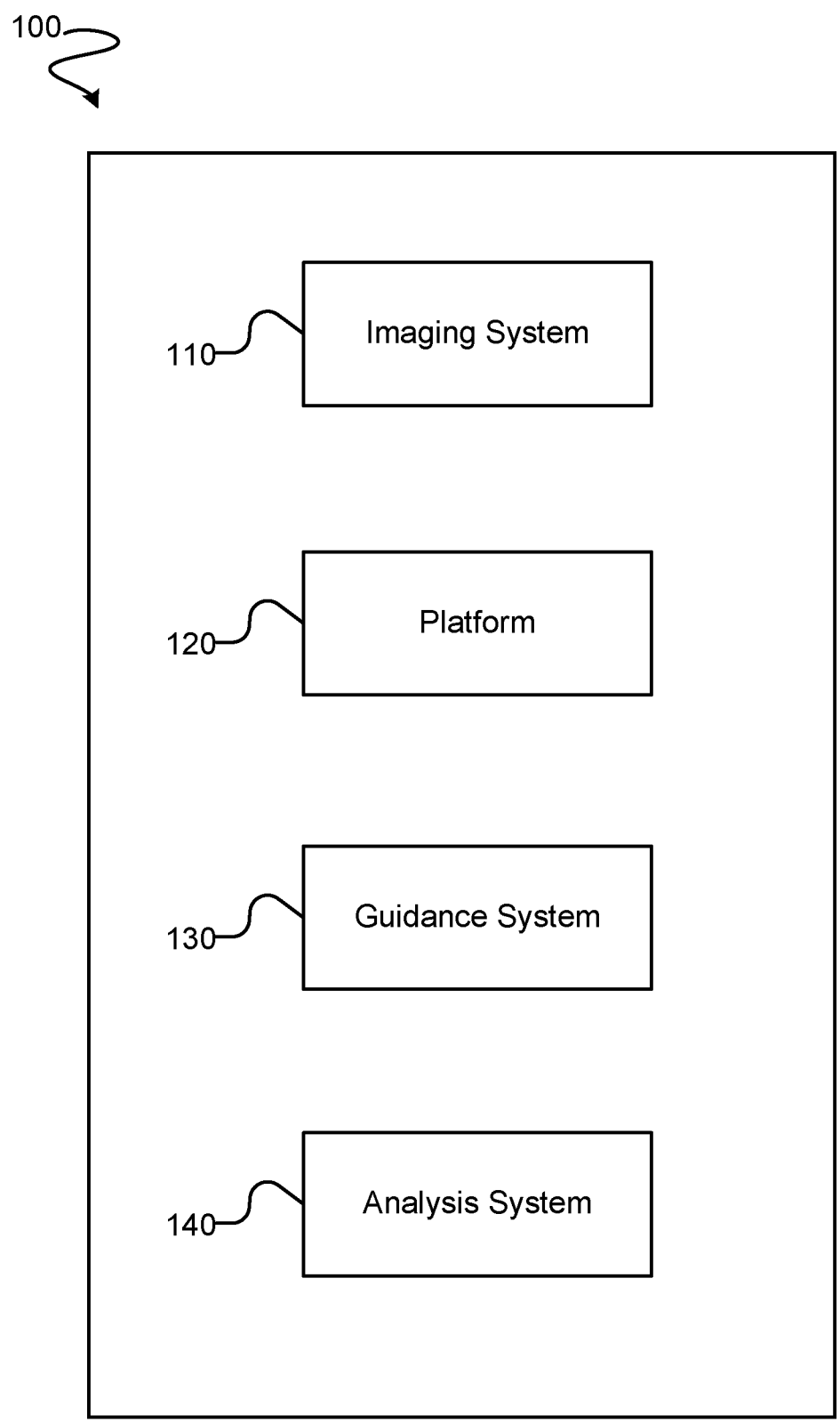
FIG. 1A depicts a system for imaging a subject according to an example embodiment.

FIG. 1A depicts a system 100 for imaging a subject, for example by total body photography (TBP) of the subject. System 100 comprises: imaging system 110, platform 120, guidance system 130, and analysis system 140. Imaging system 110 is carried by platform 120. Guidance system 130 controls platform 120. Imaging system 110 captures images and provides the images to analysis system 140. Analysis system 140 processes the images provided by imaging system 110.

Imaging system 110 comprises one or more digital cameras. Example embodiments of digital cameras include:
  a digital single-lens reflex (DSLR) camera;
  a digital camera of a tablet computer, for example an Apple™ iPad;
  a digital camera of a smartphone, for example an Apple™ iPhone; and any other portable digital camera.

Where imaging system 110 comprises a smartphone or a tablet computer, platform 120 may comprise a mount to retain the smartphone or tablet computer. In some embodiments, platform 120 may comprise a light deflector, for example a mirror or a prism, to direct light to a digital camera of the smartphone or tablet computer. The light deflector may be configured to direct light perpendicular to the digital camera of the smartphone or tablet computer.

In some embodiments, the smartphone or tablet computer may be mounted to platform 120 with a face of the smartphone or tablet computer facing upward from the ground or downward towards the ground. Mounting a smartphone or tablet computer to platform 120 with a face of the smartphone or tablet computer facing upward from the ground or downward towards the ground may improve the stability of platform 120. Platform 120 may comprise a light deflector to direct light into the camera of the smartphone or tablet computer. The light deflector may direct light traveling horizontal to the ground into the camera of the smartphone or tablet computer.

In some embodiments, platform 120 comprises a propulsion system and is partially or entirely self-propelled by the propulsion system. Where platform 120 comprises a propulsion system, guidance system may 130 control the propulsion system of platform 120. In such embodiments, platform 120 is at least partially controlled by guidance system 130 controlling the propulsion system of platform 120.

Example embodiments of platform 120 which comprise a propulsion system and are at least partially self-propelled include:
   an unmanned aerial vehicle (UAV);
   an unmanned ground vehicle (UGV);
   a motorized circular stand; and
   any motorized device capable of carrying an imaging system.

In some embodiments, platform 120 is partially or entirely propelled by a user. Where platform 120 is at least partially propelled by a user, guidance system 130 provides human perceptible instructions to the user for controlling platform 120. Human perceptible instructions provided by guidance system 130 may include audio and/or visual instructions, for example audio cues, light cues, synthesized speech, pre-recorded messages, text instructions, vibration feedback, and the like.

Examples of platform 120 which are at least partially propelled by a user include:
   a flash light case;
   a portable stand; and
   any device which may be manually manipulated by a user.

Imaging system 110 may further comprise a light source, for example one or more light emitting diodes, incandescent lamps, and/or fluorescent lamps. The light source of imaging system 110 may further comprise one or more filters configured to selectively transmit light of a certain polarity and/or spectrum. The filters may comprise one or more polarizing filters, and/or one or more optical filters. The light source and any other optical elements of imaging system 110 may be used by imaging system 110 to capture images, for example to illuminate a subject to photograph.

In some embodiments, platform 120 is integrated with imaging system 110, for example a UAV or a UGV with an integrated camera. In some embodiments, imaging system 110 is removably mounted to platform 120, for example a a UAV or a UGV with a removably mounted smartphone.

Where a propulsion system of platform 120 is at least partially controlled by guidance system 130, guidance system 130 may comprise one or more modules which control the movement, position, and/or orientation of platform 120. In some embodiments, guidance system 130 is integrated with imaging system 110. For example, imaging system 110 may comprise a smartphone and one or more modules of guidance system 130 may be implemented by the smartphone.

Where one or more modules of guidance system 130 are implemented by a smartphone, the smartphone may be communicatively coupled to the platform by a wired interface, for example a Lightning™ or USB cable. The modules of guidance system 130 may be downloaded to the smartphone by downloading a mobile app. For example, a user may access an app store from the smartphone, and then download and run a mobile app. A mobile app is a software application designed to run on a smartphone. A mobile app may be downloaded from an app store, which is an online database of mobile apps. The smartphone may comprise a memory storing the mobile app.

Guidance system 130 may control platform 120 to:
   translate platform 120 by a certain distance in a certain direction;
   roll platform 120 by a certain angle in a certain direction;
   pitch platform 120 by a certain angle in a certain direction; and/or
   yaw platform 120 by a certain angle in a certain direction.
By translating, rolling, pitching, and yawing platform 120, guidance system 130 may navigate platform 120 to any position and/or orientation.

Where platform 120 is at least partially controlled by a user, guidance system 130 may comprise one or more systems which provide instructions to a user controlling platform 120. Instructions provided by guidance system 130 to control platform 120 may include:
   an instruction to translate platform 120 by a certain distance in a certain direction;
   an instruction to rotate platform 120 by a certain angle in a certain direction;
   an instruction to pitch platform 120 by a certain angle in a certain direction; and/or
   an instruction to yaw platform 120 by a certain angle in a certain direction.

Where instructions provided by guidance system 130 to a user of platform 120 include audio cues, providing the instructions may comprise playing a pre-recorded message, for example a message such as "lower the platform by one meter", or "rotate the platform around the subject by 45 degrees".

Where instructions provided by guidance system 130 include visual cues, platform 120 may comprise one or more visual outputs, for example a liquid crystal display (LCD) or a set of LEDs arranged around a periphery of platform 120. Where platform 120 comprises a visual display, guidance system 130 may display instructions via the visual display. Example instructions displayed by the visual display may include:
   text instructing a user to move, rotate, pitch and/or yaw platform 120 about a subject;
   diagrams depicting moving, rotating, pitching, and/or yawing platform 120 about a subject; and/or
   videos depicting moving, rotating, pitching, and/or yawing platform 120 about a subject.

Where platform 120 comprises a smartphone or tablet computer, audio instructions may be provided by a speaker of the smartphone and/or tablet computer, and visual instructions may be provided by a display of the smartphone and/or tablet computer.

Guidance system 130 may also be in communication with imaging system 110 and control imaging system 110 to:
- capture a digital image with a digital camera of imaging system 110;
- set one or more photography parameters of imaging system 110, for example one or more of an aperture size, shutter speed, ISO sensitivity, and focal length of a digital camera of imaging system 110; and/or
- set an intensity and/or spectrum of light emitted by a light source of imaging system 110.

To control platform 120 and/or to generate instructions for a user to control platform 120, guidance system 130 may determine and/or store:
- a layout of markers (described below);
- a current position and/or orientation of platform 120;
- a current position and/or orientation of a subject;
- a current position and/or orientation of a subject relative to a current position and/or orientation of platform 120;
- a current position and/or orientation of one or more objects relative to a current position and/or orientation of platform 120; and/or
- a previous position and/or orientation of platform 120 relative to a subject.

Guidance system 130 may comprise one or more modules including:
- a localization module configured to determine a location and/or an orientation of platform 120;
- a navigation module configured to determine a photography scheme (described below) for platform 120 and imaging system 110;
- an obstacle avoidance module configured to control platform 120 to avoid one or more obstacles;
- a skeletal detection module configured to generate a skeletal map of a subject;
- a face detection module configured to determine a position and/or orientation of a face of a subject;
- a face recognition module configured to identify a face of a subject; and/or
- an image stabilization module configured to stabilize a digital camera of imaging system 110.

Guidance system 130 may comprise one or more inputs, for example one or more sensors. Examples of sensors comprising guidance system 130 include:
- Light Detection and Ranging (LIDAR) sensors;
- infrared range finder sensors;
- digital cameras;
- inertial measurement (IMU) sensors such as gyroscopes and accelerometers;
- ultrasonic range finder sensors;
- RADAR;
- GPS;
- electromagnetic sensors;
- barometric pressure sensors; and/or
- optical flow sensors.

In some embodiments, one or more digital cameras of imaging system 110 may also be used by guidance system 130 to generate inputs for guidance system 130.

Images captured by imaging system 110 are transmitted to analysis system 140. Analysis system 140 comprises one or more modules which may receive and/or analyze images from imaging system 110. Examples of modules of analysis system 140 include:

- a 3D model construction module;
- a lesion/spot analysis module; and/or
- an automated lesion/spot detection module.

Figure 1B:
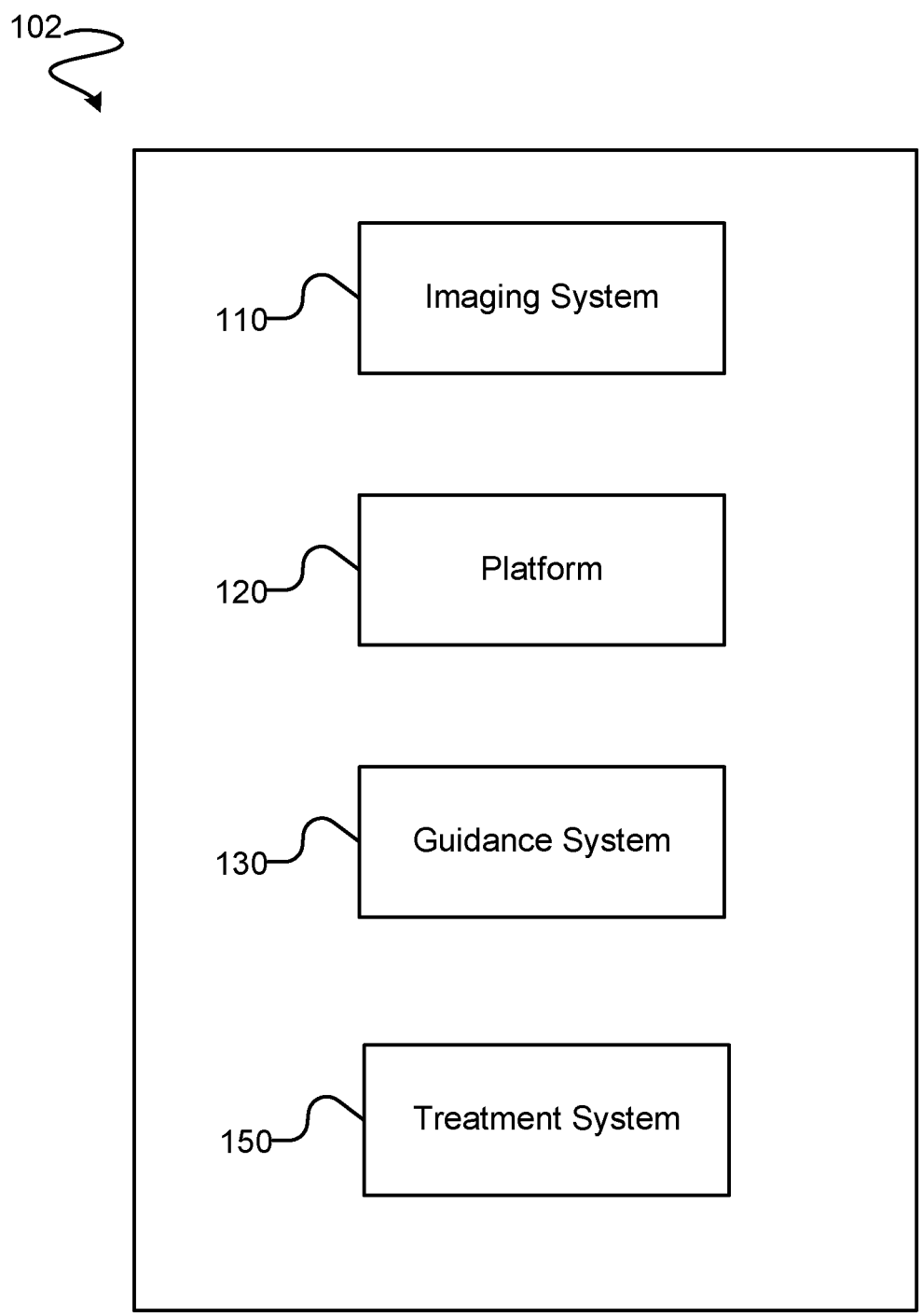
FIG. 1B depicts a system for administering photodynamic therapy to a subject according to an example embodiment.

FIG. 1B depicts a system 102 for administering photodynamic therapy to a subject. System 102 comprises: imaging system 110, platform 120, and guidance system 130, similar to system 100 described above.

System 102 further comprises treatment system 150. Treatment system 150 comprises one or more light sources configured to emit light for administering photodynamic therapy. In some embodiments, treatment system 150 comprises one or more light emitting diodes (LEDs) for administering photodynamic therapy.

In some embodiments, treatment system may be configured to administer photodynamic therapy according to a photodynamic therapy scheme. Treatment system 150 may be configured to generate the photodynamic therapy scheme at least in part based on:
- a location of platform 120;
- an orientation of the platform 120;
- a location of the subject;
- an orientation of the subject; and
- a photodynamic therapy prescription.

The photodynamic therapy prescription may comprise a photodynamic therapy region and a photodynamic therapy light dose. The photodynamic therapy region may correspond to a region of a subject, for example a lesion of a subject.

The photodynamic therapy scheme generated by treatment system 150 may comprise a set of photodynamic control points, wherein each of the photodynamic control points comprises:
- a location of platform 120;
- an orientation of platform 120;
- an illumination intensity; and
- an illumination time.

The photodynamic control points may be generated by treatment system 150 by first determining the location and the orientation of platform 120 required to illuminate the photodynamic therapy region. Once the location and the orientation of platform 120 required to illuminate the photodynamic therapy region is determined, treatment system 150 may determine the illumination intensity and illumination time required to deliver the photodynamic therapy prescription to the photodynamic therapy region from the location and the orientation of platform 120.

Where platform 120 is at least partially self-propelled, treatment system 150 may control platform 120 and direct platform 120 to each of the photodynamic therapy control points and control the light source of treatment system 150 to illuminate the photodynamic therapy region of the subject with light of the illumination intensity and for the illumination time.

An aspect of the invention provides an UAV capable of acquiring high resolution two-dimensional (2D) and/or three-dimensional (3D) body surface images, including images of skin, hair, and nails. The UAV provides a low-cost solution for TBP that is suitable for indoor use at skin clinics, medical offices, hospitals, pharmacies, home, etc.

An unmanned aerial vehicle (UAV) (also known as a drone) is an aircraft without an onboard human operator. An UAV is typically one component of an UAV system, which includes the UAV, a controller, and a communication system between the UAV and the controller. An UAV may operate under remote control by a human operator or autonomously by one or more onboard computers.

Images may be acquired by the UAV in 2D or 3D. In some embodiments, the UAV is used to acquire 3D body surface images directly in 3D with a 3D camera, or by merging position-known 2D images acquired by navigating the UAV around an object to be imaged. The images may be a series of 2D or 3D images, which may be combined to form a 3D representation of the imaged body.

In some embodiments, the UAV includes a digital camera for acquiring images. The UAV may include one or more sensors, LED cross-polarized lighting, and/or an onboard computer system (i.e. hardware and software) capable of real-time image acquisition, storage, and/or analysis. In some embodiments, the UAV may transmit images wirelessly to an external computer system to analyze the images acquired by the UAV.

In some embodiments, the position and/or location of the UAV may be determined in real-time. The UAV may be maneuvered automatically to specific locations to capture desired images. In this way, the UAV is capable of taking reproducible images. Such images are useful for TBP. When such images are taken over time, comparisons between such images may be further useful for TBP.

In some embodiments, the UAV includes means for stabilizing the UAV. For example, the UAV may comprise one or more stability sensors such as gyroscopes and/or accelerometers to measure the tilt, rotation, and/or pitch of the UAV. Such measurements of tilt, rotation, and/or pitch may be used to stabilize the UAV. By stabilizing the UAV, high quality images may be acquired. Such images may be useful for TBP.

In some embodiments, the UAV may be used to acquire full-body or partial-body surface images. Such images may be used and analyzed for automated screening of skin conditions, for example automated screening for skin cancer, pigmented lesions, and/or vascular lesions. In addition, the UAV may be used to analyze other skin conditions, such as acne, rashes and inflammatory diseases such as psoriasis or eczema. The UAV may be used to estimate the size and coverage of the disease area as well as to estimate the depth of the condition (for example wrinkles, raised lesions, wounds, etc.), to monitor a condition on different body parts, and/or to monitor treatment progress. The UAV may be used for cosmetic and/or plastic surgery applications and/or may be used by dermatologists, surgeons, general practitioners, nurses, photographers, and consumers/patients.

In some embodiments, the UAV may be used by a user to acquire an overview image of a patient's body or body part. In some embodiments, the UAV may be used to identify and image a body or body part, detect skin lesions in the acquired image, and label and place the lesions on a 2D or 3D body map.

In some embodiments, the UAV may be used to automatically identify areas of interest of the skin such as acne, rashes, psoriasis, eczema and wounds, and place them on a 2D or 3D body map for labelling, archiving and monitoring over time.

In some embodiments, the UAV may be used to analyze skin lesions on a real-time basis. Onboard and/or external computer systems may be used to instruct the UAV to reimage and/or get closer to a lesion to take higher quality images.

In some embodiments, the UAV is equipped with a dermoscope to take dermoscopy images. The dermoscopy images may be any combination of polarized/non-polarized/cross-polarized images.

Figure 2A:
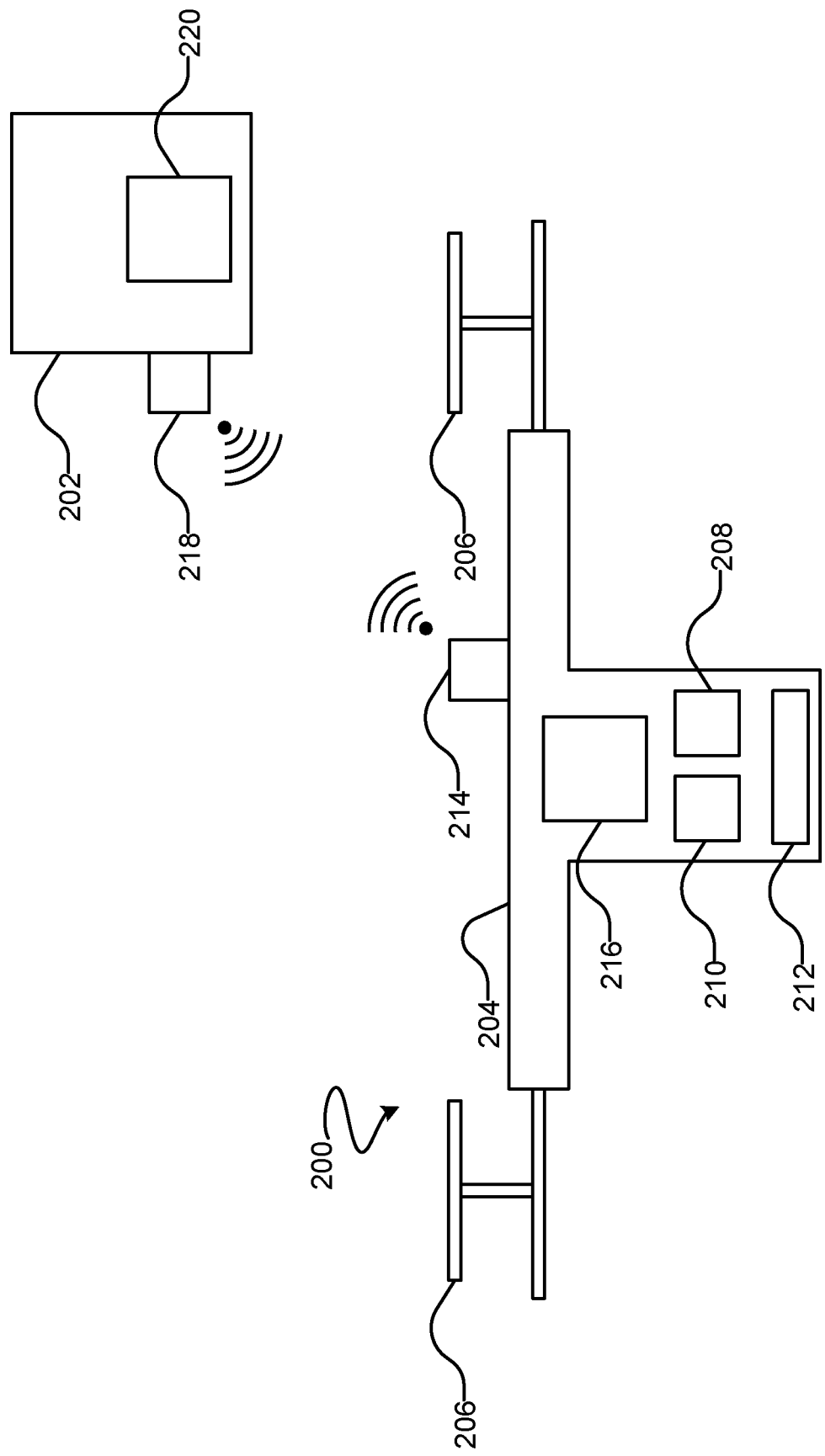
FIG. 2A depicts a system according to an example embodiment.

FIG. 2A depicts an embodiment of imaging system 110 and platform 120 comprising unmanned aerial vehicle (UAV) 200 and controller 202.

UAV 200 comprises body 204 and rotors 206. UAV 200 is lifted and propelled by rotors 206.

UAV 200 further comprises digital camera 208 and light source 210. Light source 210 is configured to illuminate a subject, and digital camera 208 is configured to capture one or more digital images of the illuminated subject. In some embodiments, light source 210 emits polarized light.

UAV 200 further comprises one or more sensors 212, transceiver 214, and onboard computer 216. Computer 216 comprises a memory and a processor. Computer 216 is communicatively coupled to digital camera 208, light source 210, sensors 212, and transceiver 214.

Controller 202 comprises transceiver 218 and computer 220. Computer 220 comprises a processor and a memory storing software to be executed by the processor. UAV transceiver 212 and transceiver 218 are configured to wirelessly communicate with each other, for example by the MAVLink™ communication protocol.

Sensors 212 may comprise one or more devices capable of measuring a parameter of the environment proximate UAV 200, for example one or more of: LIDAR sensors, infrared range sensors, digital cameras, ultrasonic range sensors, accelerometers and an indoor-GPS transmitter (described below).

Computer 216 is configured to receive sensor data from sensors 212. Computer 216 may control rotors 206 in part based on sensor data received from sensors 212. For example, computer 212 may control rotors 206 to navigate UAV 200 to avoid an obstacle, for example to avoid a wall, ceiling, floor, object or person.

Computer 216 is configured to control transceiver 214 to transmit sensor data to controller 202 via transceiver 218. Computer 220 may be configured to receive sensor data from transceiver 218.

Computer 220 is configured to control UAV 200, and control transceiver 218 to transmit commands to UAV 200 via transceiver 214. Computer 216 may receive commands from transceiver 214 and control rotors 206 to navigate UAV according to the command.

Computer 220 may generate commands for controlling UAV 200 based in part on one or more of: received sensor data, stored images, and user input. For example, computer 220 may generate one or more commands to:
  control rotors 206 to navigate UAV about a subject, and orient light source 210 and digital camera 208 relative to the subject;
  control light source 210 to illuminate the subject; and
  control digital camera 208 to photograph the subject.

Computer 216 may be configured to control transceiver 214 to transmit digital images generated by digital camera 208 to controller 202 via transceiver 218. Computer 216 may be configured to store digital images generated by digital camera 208 in a memory, for example a flash memory card.

Figure 2B:
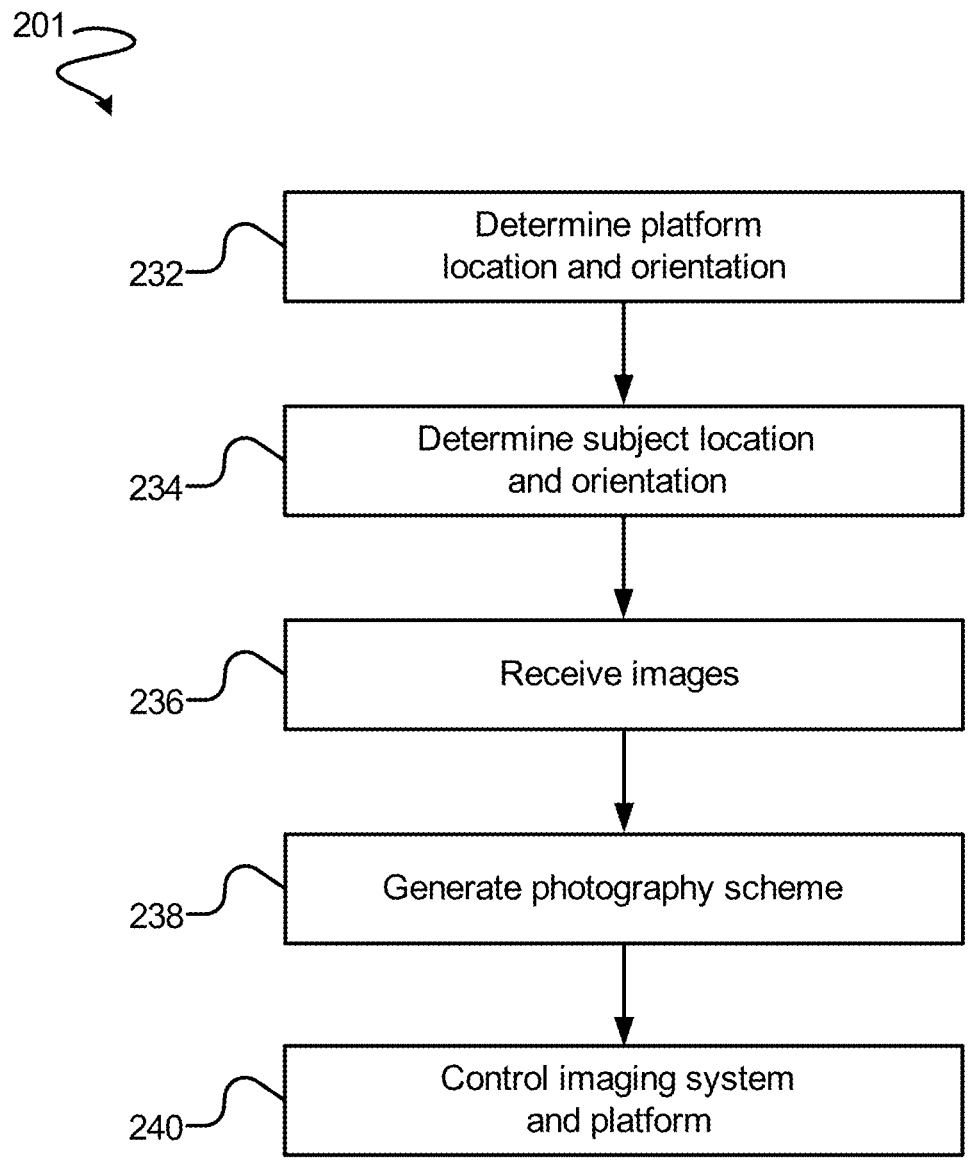
FIG. 2B depicts a method for imaging a subject according to an example embodiment.

FIG. 2B depicts an example method 201 performed by UAV 200 and controller 202 for photographing a subject. Prior to performing method 201, the subject may be positioned in a pre-determined location. For example, the subject may be a person, and the person may be instructed to stand in a specified location with a specified posture. For example, the person may stand upright with their feet placed on a specific location and with their hands grasping handles fixed proximate the specific location.

Method 201 comprises:

step 232: determine a location and an orientation of UAV 200;

step 234: determine a location and an orientation of a subject;

step 236: receive one or more images of the subject;

step 238: generate a photography scheme; and step 240: control UAV 200 according to the photography scheme.

The location of UAV 200 may be determined in step 232 for example by UAV photographing at least one marker in a network of markers, and computer 220 determining the location of UAV 200 from the photographed marker, as described below. The position of UAV 200 may be stored in the memory of computer 220. The position of UAV 200 may be represented by a location vector representing a direction and distance from a certain location. For example, one marker in the network of markers may be designated as a prime marker, and all other location vectors may represent a direction and distance from the prime marker.

The orientation of UAV 200 may be determined in step 232 by determining an orientation of the photographed marker. To determine the orientation of a photographed marker, computer 220 may determine a rotation of the photographed marker from an orientation of a known marker. For example, computer 220 may determine that a photographed marker is rotated a certain degree from a known marker. If digital camera 208 is mounted at a known position on UAV 200, then the orientation of UAV 200 can be determined from the certain degree of rotation of the photographed marker.

For example, a known marker may have a known orientation relative to the prime marker. Computer 220 may determine a rotation of a photographed marker relative to the known marker, and thereby determine a rotation of the photographed marker relative to the prime marker. Computer 220 may then determine a rotation of UAV 200 relative to the prime marker from the rotation of the photographed marker relative to the prime marker.

The location and orientation of the subject may be determined in step 234 by positioning and orientating the subject in a pre-determined location, and storing the pre-determined location of the subject in the memory of computer 220. For example, where the subject is a person, the person may be positioned by standing on a certain marker, designated a subject marker, in the network of markers. Computer 220 may store the position of the subject marker as a location vector representing a direction and a distance from the prime marker.

The person may be positioned at the subject marker in a certain orientation by having the person assume a certain posture at the subject marker. For example, the person may be instructed to: stand, sit or lie down, and/or grasp a handle fixed proximate the subject marker, and/or arrange their limbs in a certain manner. For example, the person may be instructed to stand upon the subject marker with their body erect and with their hands at their sides.

The person to be photographed may be instructed to assume a posture at the subject marker corresponding to a position and an orientation of a representative person. Computer 220 may store a position and an orientation of the representative person as a three dimensional (3D) model. The 3D model of the representative person may represent the position of major features of the representative person. For example, the 3D model may include location vectors for each of the representative person's major body parts. Such major body parts may include the representative person's head, chest, arms and legs. The body part location vectors may be represented as location vectors relative to the prime marker.

The one or more images of the subject may be received in step 236 by computer 220 retrieving the images from the memory of computer 220. Such images may have been captured previously by UAV 200. The images may include associated metadata, for example one or more photography parameters (described below) and a location and/or orientation of UAV 200 used to capture an image. The location and/or orientation of UAV 200 may be represented as a location vector indicating a direction and distance from the prime marker.

Step 238 may comprise generating a photography scheme based at least in part on:

the location of UAV 200;

the orientation of UAV 200;

the location of the subject;

the orientation of the subject; and the one or more images of the subject.

In some embodiments, the photography scheme comprises a set of photography control points, each of the photography control points comprise:

a location of UAV 200;

an orientation of UAV 200; and one or more photography parameters.

The one or more photography parameters may include one or more of: a shutter speed; an aperture size; a focal length; an ISO sensitivity; and an illumination level.

To generate the photography scheme, computer 220 may determine a number of images required of the subject. For example, computer 220 may determine that thirty images of the subject are required, where ten images are taken at a first elevation, ten images are taken at a second elevation greater than the first elevation, and ten images are taken at a third elevation greater than the second elevation. Each of the ten images at each elevation may be separated by an equal angle about the subject. For example: a first image may be taken at a starting position, a second image may be taken at a second position 36° around the subject from the starting position, a third image may be taken at a third position 72° around the subject from the starting position, and so on with each image being taken at a position (n×36°) around the subject from the starting position, where n is an index identifying the image with 0≤n≤9 in this example.

Once computer 220 has determined the number of images of the subject required, computer 220 may determine the photography control points required to capture each of the required images. For example, computer 220 may determine a position and an orientation of drone 200 required to capture each of the thirty images referenced above. To determine the position and orientation of drone 200 required to capture each image, computer 220 may determine a distance from the subject for each image. The distance from the subject for each image may be represented as an image vector with a direction and distance from the subject marker. The set of image vectors may then be used to generate the set of photography control points specifying the location and orientation of UAV 200 required to capture each of the required images.

Computer 220 may generate one or more photography parameters for each of the photography control points. For example, computer 220 may set a focal length and an aperture size of a photography control point to capture a certain depth of field a certain distance from drone 200. The distance of the depth of field from drone 200 may be approximately equal to a distance from the subject to drone 200 when drone 200 is at the location and orientation of the respective photography control point. The depth of field may be approximately equal to the depth of the subject. In some embodiments the depth of field may be 1 meter.

Computer 220 may also set a shutter speed and ISO sensitivity for each of the photography control points. Computer 220 may set the shutter speed and ISO sensitivity of a photography control point as a function of the focal length and aperture size of the photography control point. For example, computer 220 may set the shutter speed and ISO sensitivity of a photography control point to produce a certain exposure level. An exposure level approximates the amount of light reaching digital camera 208, which affects the brightness of an image captured by digital camera 208.

Computer 220 may modify the photography control points based on one or more previous images of the subject. For example, computer 220 may determine that a previous image of the subject was taken by drone 200 at a certain location and with a certain orientation. Determining the location and orientation of drone 200 used to capture the previous image may comprise reading metadata associated with the previous image. Computer 220 may then select one of the photography control points with the nearest position and orientation to the position and orientation of the previous image, and modify the location and orientation of the selected photography control point to more closely match the position and orientation of the previous image.

Computer 220 may modify the photography control points based on one or more previous images of the subject by adding a photography control point. The added photography control point may have the same location, orientation, and photography parameters as the location, orientation, and photography parameters of a previous image of the subject.

In some embodiments, a user may select a previous image of the subject to be reproduced. The user may select the previous image from a database of previous images using an interface of computer 220. Computer 220 may then add a photography control point with the same location, orientation, and photography parameters as the location, orientation, and photography parameters of the selected image of the subject.

Controlling UAV 200 according to the photography scheme in step 240 may comprise controller 202 determining commands to navigate UAV 200 between a current position and orientation of UAV 200 and a position and an orientation of one of the photography control points, and controlling UAV 200 to navigate UAV 200 to one of the photography control points. The commands determined by controller 202 may include commands to operate the rotors of UAV 200 to navigate UAV 200. For example, controller 202 may increase power to one or more of the rotors of UAV 200 to move UAV 200 in a certain direction.

Once controller 202 determines that UAV 200 is at one of the photography control points, controller 202 may control digital camera 208 to capture a photograph according to one or more photography parameters associated with the one of the photography control points.

Computer 220 may modify one or more photography control points based on sensor data acquired while controlling UAV 200 according to the photography scheme in step 240. For example, sensors 212 may comprise a LIDAR sensor configured to measure a distance from UAV 200 to the subject. Once UAV 200 is at a photography control point, the LIDAR sensor may determine a distance between UAV 200 and the subject. Computer 220 may then modify one or more photography parameters of the photography control points based on the distance between UAV 200 and the subject. For example, computer 220 may determine an aperture size and/or focal length required to capture an image of the subject at the distance between UAV 200 and the subject. Computer 220 may then modify the aperture size and/or focal length of the photography control point according to the determined aperture size and/or focal length.

UAV 10 according to an example embodiment of the present invention is shown in FIGS. 3A-3E. An alternative embodiment, UAV 11, is shown in FIGS. 4A-4D. Many features and components of UAV 10 are similar to features and components of UAV 11, with the same reference numerals being used to indicate features and components that are similar between the embodiments. UAV 10, 11 is used to capture images and may be employed in a variety of indoor or outdoor applications. In some embodiments, UAV 10, 11 is used to capture images of a subject. For example, UAV 10, 11 may be used to capture images of a patient's body or part thereof. The captured images may be used to detect, monitor, diagnose, and monitor treatment of skin, hair, and/or nail features, conditions, and/or diseases. UAV 10, 11 may be used indoors, for example in healthcare, professional offices, hospitals, private homes, etc.

UAV 10, 11 is a multirotor drone that is lifted and propelled by rotors (i.e. horizontally-oriented propellers). In the embodiments illustrated in FIGS. 3A-4D, UAV 10, 11 comprises a quadcopter having a body 12, four arms 14 extending outwardly from the body, and a rotor 16 coupled to each arm. UAV 10, 11 may comprise any number of rotors capable of lifting and propelling UAV 10, 11. In some embodiments, UAV 10, 11 may comprise one or more rotor guards. In the embodiment illustrated in FIGS. 3A-3E, UAV 10 comprises rotor guard 18 sized and positioned above rotors 16 to protect the rotors and/or to prevent rotors 16 from causing damage should the UAV collide with a user, bystander, and/or other object.

In some embodiments, UAV 10, 11 may comprise three, four, or more coaxial rotors capable of lifting and propelling UAV 10, 11.

To capture images, UAV 10, 11 comprises imaging system 20. Imaging system 20 includes at least one camera 30 and at least one light source 40. In some embodiments, camera 30 houses at least one light source 40. In the embodiments illustrated in FIGS. 3A-4D, camera 30 is mounted to a front surface 12a of body 12 and light source 40 is mounted to a bottom surface 12c of body 12. Camera 30 and/or light source 40 may be mounted on alternative positions of body 12. In some embodiments, camera 30 and/or light source 40 is mounted on body 12 using a gimbal (not shown). The gimbal may permit camera 30 and/or light source 40 to pivot about one, two, or three axes. In some embodiments, the gimbal may permit camera 30 to pivot about one, two, or three axes to reduce the effect of propeller vibration on image quality and/or to orient camera 30 for capturing an image.

Camera 30 is a digital camera that captures high-quality images. High-quality images may be images with a resolution of at least 12-megapixels. In some embodiments, images are captured and stored in the digital memory (e.g. SD card) of camera 30 and/or are captured and wirelessly transmitted to external memory of cloud computing or other external computing devices via WiFi, satellite, and/or mobile connection. One or more photography parameters of camera 30 such as shutter speed, aperture length, focal length and ISO sensitivity, may be selected such that a desired magnification of an object with minimal optical distortion is acquired. For example, in some embodiments, the focal length of camera 30 is between about 15 and about 35 mm and/or the optical magnification of camera 30 is between about 1.5× and 2×. In some embodiments, camera 30 comprises a 12-megapixel CMOS sensor and 24 mm f/2.8 lens with a 35 mm-equivalent focal length.

Imaging system 20 may comprise one or more optical elements, such as lenses, films, filters, diffusers, and polarizers (e.g. linear polarizers, circular polarizers, etc.) for improving image quality and/or for acquiring magnified images. Imaging system 20 may comprise a plurality of lenses. Each lens (not shown) may for example comprise a double-convex lens, a plano-convex lens, a Fresnel lens, a doublet lens, an achromatic lens, or a meniscus lens. Each lens may be coated with an anti-reflection coating to improve image quality.

In some embodiments, imaging system 20 comprises one or more filters (not shown). The one or more filters may be used to filter and/or polarize the light emitted by imaging system 20 and/or the light that is reflected by an object or patient to be imaged. In some embodiments, the one or more filters may be used to achieve cross polarization for improving image quality.

Figure 3C:
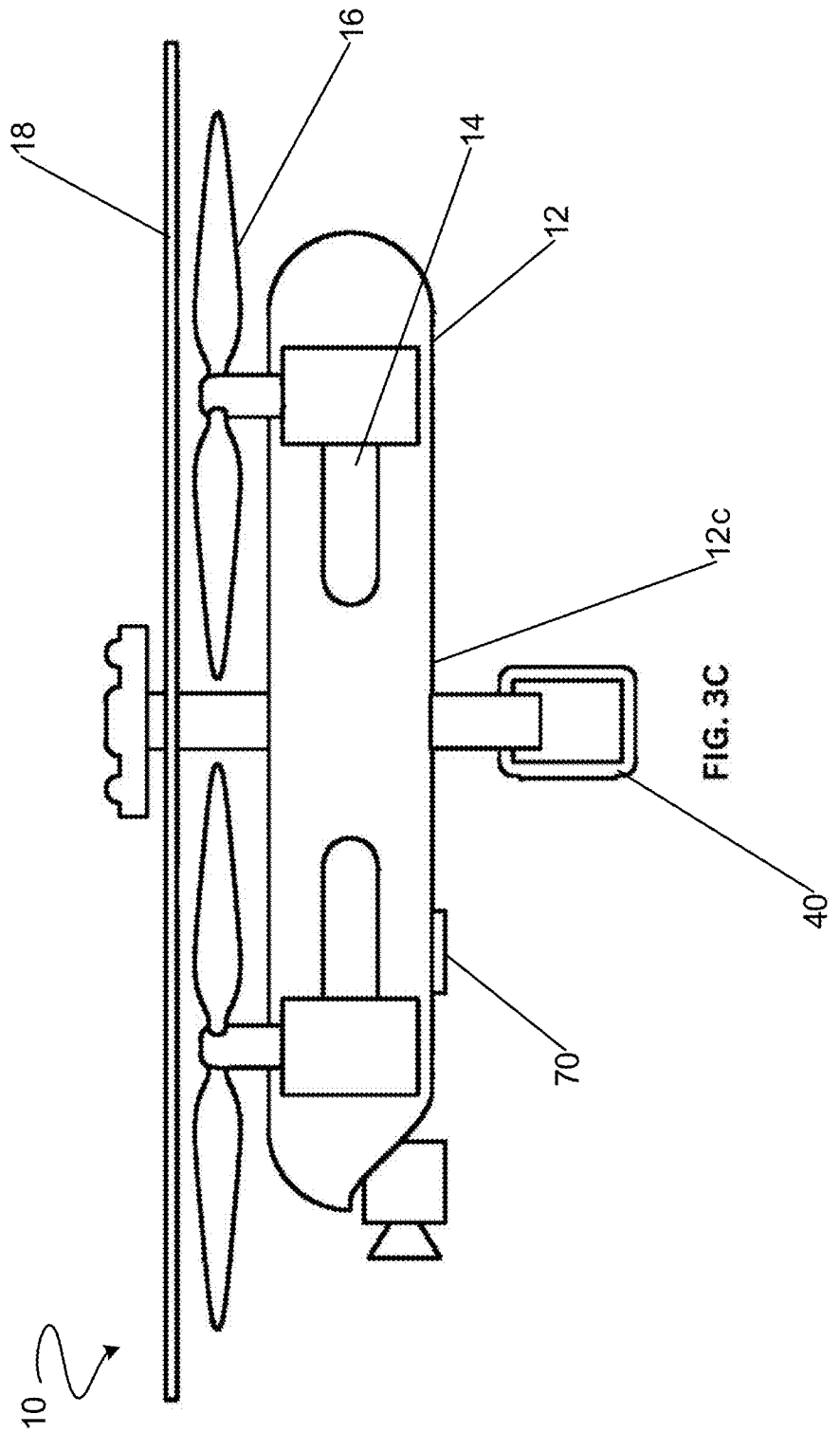
Figure 3D:
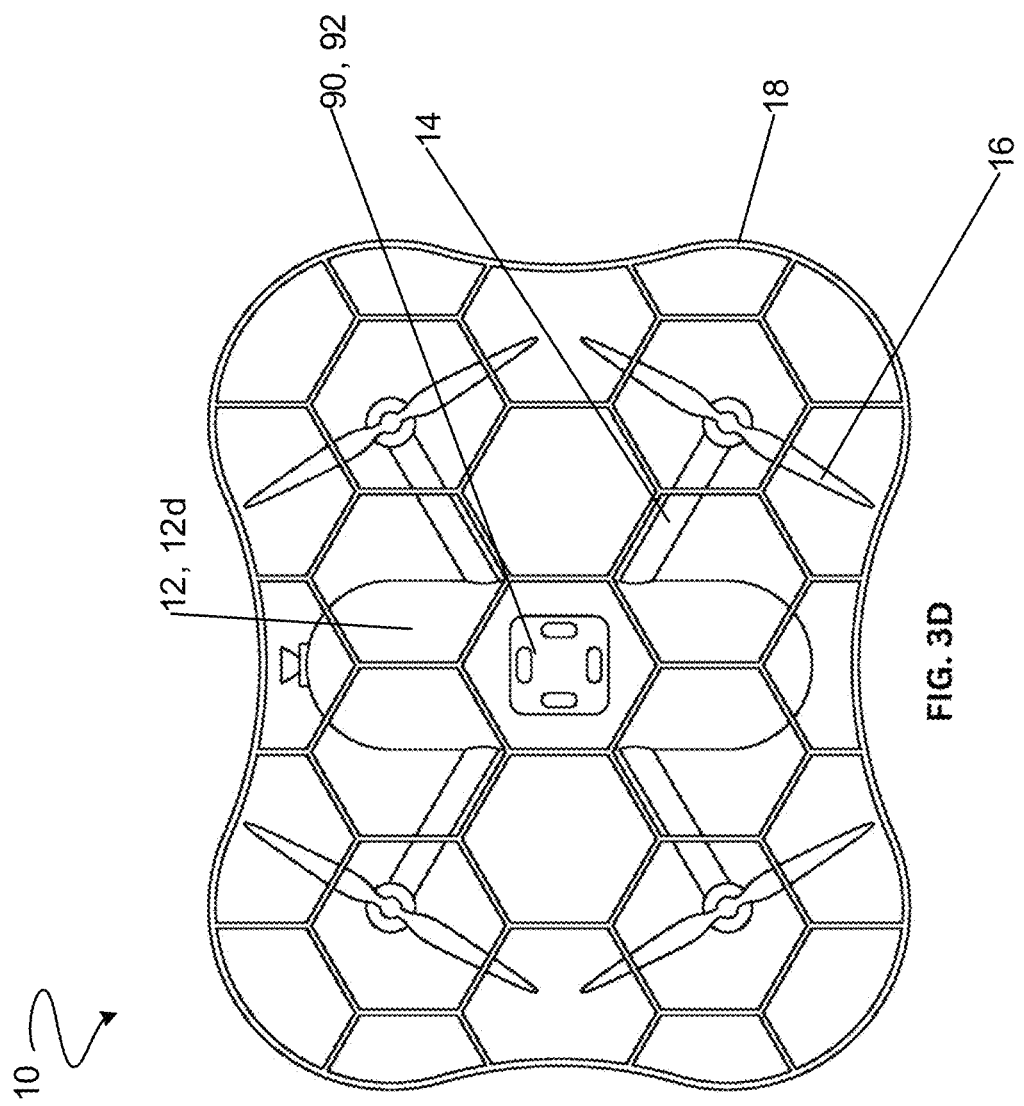
Figure 3F:
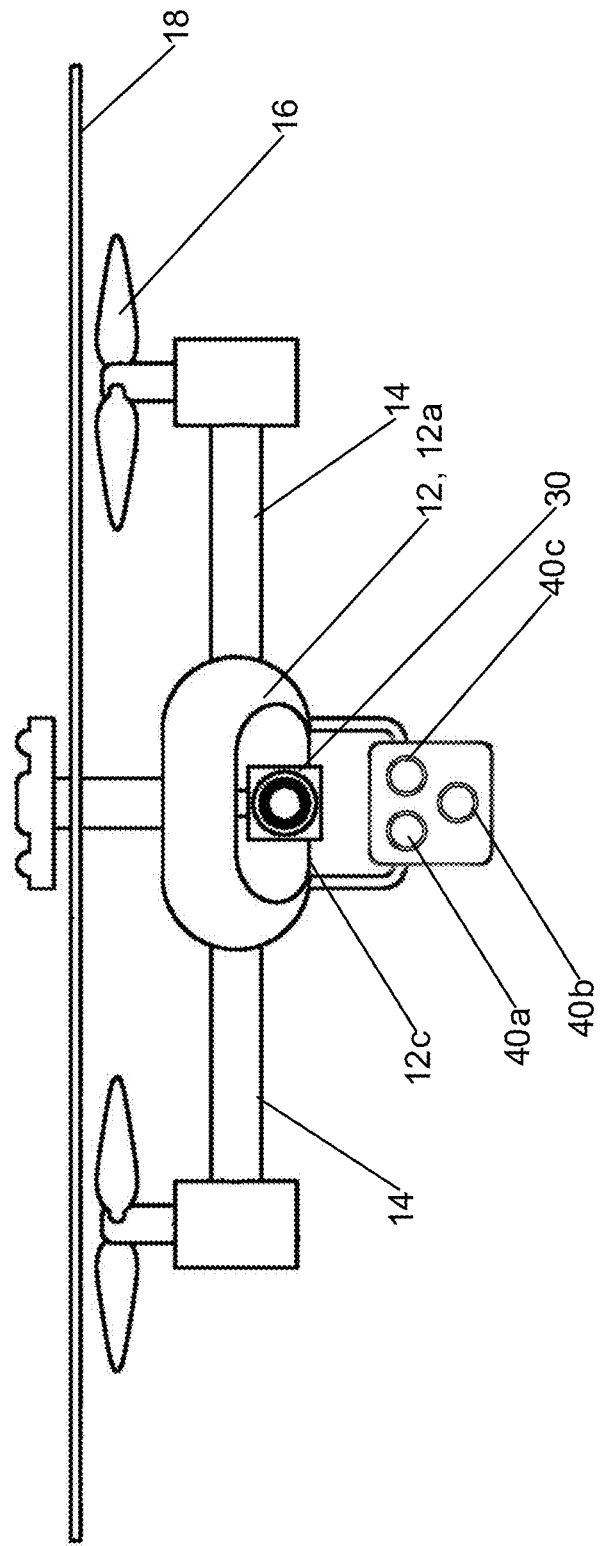
FIG. 3F depicts an unmanned aerial drone (UAV) according to an example embodiment.
Figure 4B:
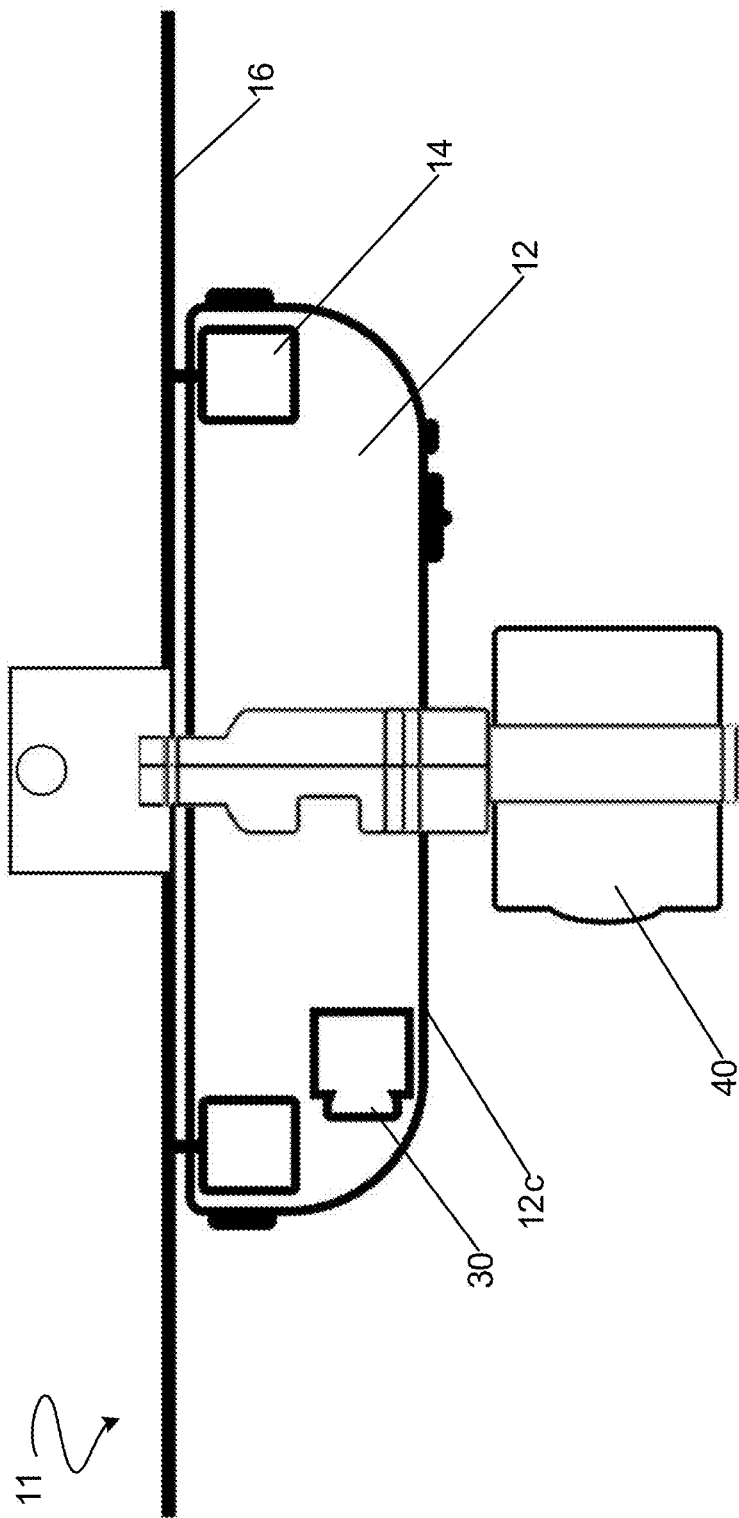
Figure 4C:
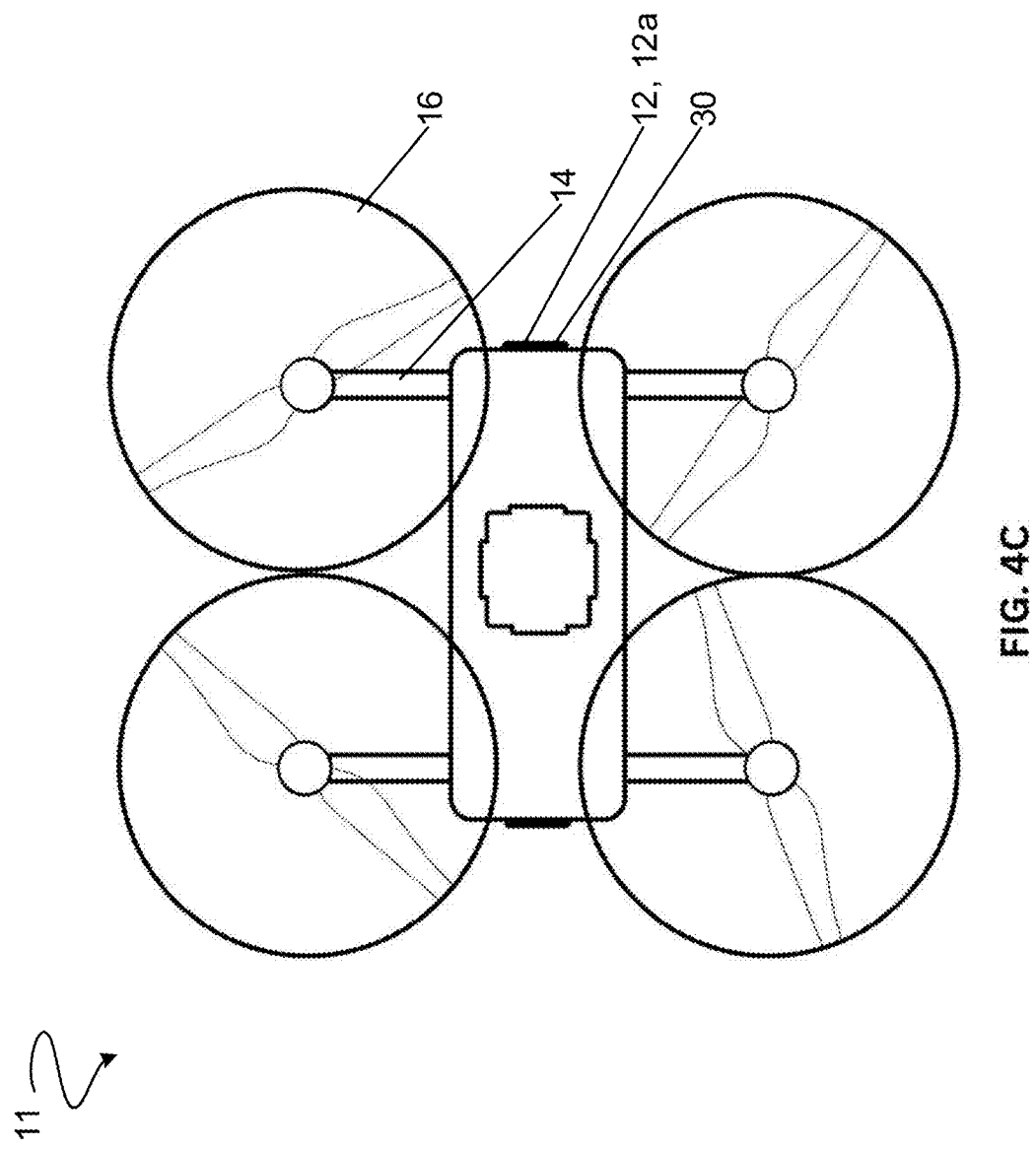
Figure 4D:
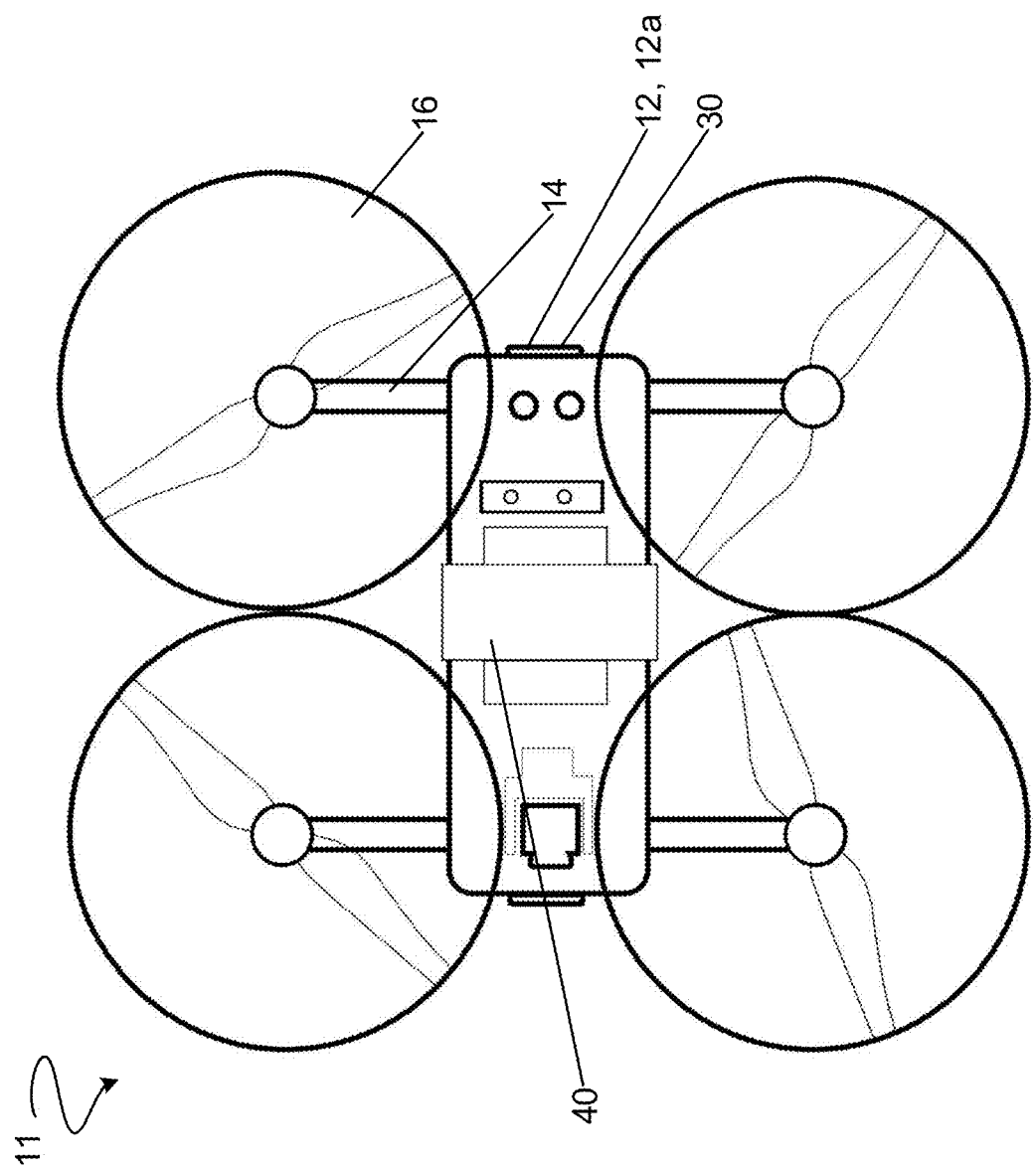

In some embodiments, imaging system 20 comprises multiple cameras having different optical specifications. For example, FIG. 3F depicts an embodiment of imaging system 20 comprising a first camera 40a to take overview images of a first image quality, a second camera 40b that has an optical zoom to take images of a second image quality, and a third camera 40c to take dermoscopic images. The quality of an image may be the resolution of the image. The photography parameters may include which camera is used to capture a certain image.

Light source 40 may comprise one or more optical elements, such as films, filters, diffusers, and polarizers (e.g. linear polarizers, circular polarizers, etc.) for improving image quality and/or for acquiring magnified images. In some embodiments, light source 40 includes one or more filters (not shown). The one or more filters may be used to filter and/or polarize the light emitted by light source 40. In some embodiments, the one or more filters may be used to achieve cross polarization.

In some embodiments, light emitted by imaging system 20 and/or light source 40 illuminates skin to be imaged. Light is reflected by the skin as specular reflection and/or by diffuse reflection. Light rays that are reflected from the surface of an object via specular reflection may create glare in the acquired image. Specular reflected light often causes the imaged skin to appear shiny. Specular reflected light interferes with the acquisition of an image showing detailed features of the skin. Specular reflected light tends to have substantially the same polarization as the incident light emitted by UAV 10, 11. In contrast, diffused light is not polarized. Since skin is partially translucent, some light hitting the surface of the skin is reflected as diffuse light by the skin's deeper layers. Diffuse light may contain useful information about the skin and its features.

In some embodiments, diffused reflected light passes through one or more filters (not shown). The one or more filters may be used to substantially block specular reflected light rays and/or remove glare and/or acquire a digital image of a feature below the surface of skin. For example, if a first filter is a linear polarizer, then to block specular reflected light rays, a second filter may be set with its polarization axis rotated 90° relative to that of the first filter. If the first filter is a circular polarizer that polarizes light in the clockwise direction, then to block specular reflected light rays, the second filter can be a circular polarizer that polarizes light in the counter clockwise direction. If the first filter is a circular polarizer that polarizes light in the counter clockwise direction, then to block specular reflected light rays, the second filter can be a polarizer that polarizes light in the clockwise direction.

In some embodiments, imaging system 20 and/or light source 40 may include a filter (not shown) for providing structured precision lighting to an object to be imaged. Structured lighting may assist in determining a depth of an imaging subject. Structured precision lighting may include emitting light in a known pattern, for example a regular grid of light. When such emitted light is reflected by an object and captured in an image, the imaged grid may be compared to the emitted grid to determine a depth of the imaging subject.

In some embodiments, UAV 10, 11 may be used to administer photodynamic therapy. For example, light source 40 may emit ultraviolet (UVA and/or UVB) light. Such embodiments may be used to reduce the symptoms of psoriasis (e.g. skin pigmentation caused by sun damage).

UVB light may penetrate the skin of a subject and slow the growth of affected skin cells. Such phototherapy with UVB light may involve exposing a subject's skin to a UVB light source for a set length of time for a set period of time.

In some embodiments, a patient may be treated by photodynamic therapy according to a photodynamic treatment scheme. System 20 may be configured to generate a photodynamic treatment scheme according to imaging of the subject.

To direct UAV 10, 11 about the subject to be imaged, UAV 10, 11 further comprises a guidance system. The guidance system may comprise an indoor global positioning (indoor-GPS) system. The indoor-GPS system may provide accurate location data (e.g. within about 2 cm) for UAV 10, 11.

The indoor-GPS system comprises a transmitter mounted to UAV 10, 11 and a network of stationary receivers (i.e. stations) positioned on the ground and/or walls about an object to be imaged by UAV 10, 11. The transmitter mounted to UAV 10, 11 and network of stationary receivers are in communication via a radio interface. The indoor-GPS system is used to determine the location of UAV 10, 11 while moving or stationary by using multiple ranges (i.e. distances) between UAV 10, 11 and the receivers which are positioned at known locations.

FIGS. 3A-4D illustrate an example embodiment of a localization module of guidance system 130 comprising an indoor-GPS, wherein the indoor-GPS comprises markers of known locations and camera 70. Camera 70 is mounted to bottom surface 12c of body 12 and oriented toward the ground. A network of markers is placed on the ground in view of camera 70. Camera 70 is positioned and oriented to acquire images of the network of markers positioned on the ground about an object. Camera 70 is a digital camera that is used to capture real-time images and/or video of the markers. Real-time images and/or video may be captured, stored, processed, and analyzed in the digital memory (e.g. SD card) of UAV 10, 11 and/or are wirelessly transmitted to an external computing system via WiFi, satellite, and/or mobile connection. The computing system then stores, processes, and analyzes the images and/or video to determine a position of UAV 10, 11.

Figure 5B:
Figure 5A:
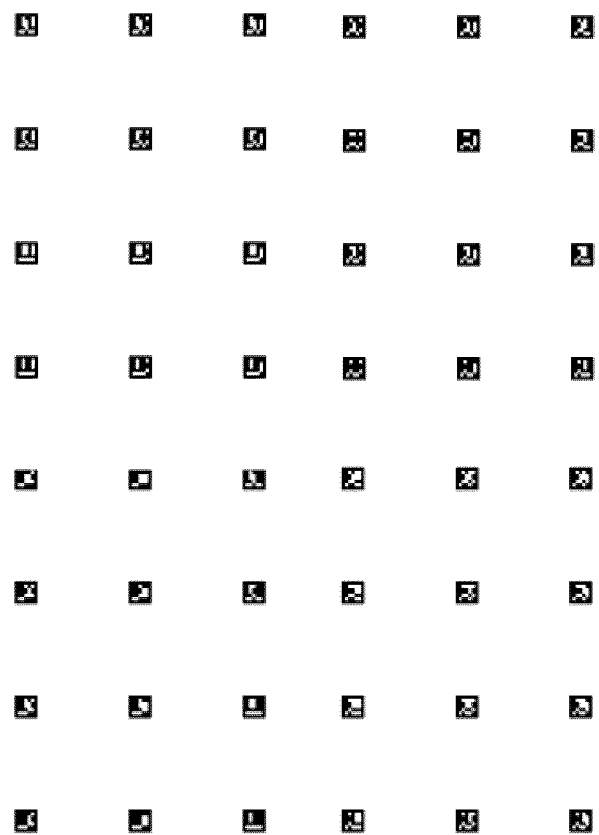

FIGS. 5A-5B illustrate a network of markers 80 of a localization module according to an example embodiment. Network of markers 80 comprises multiple markers 82 arranged in a grid pattern. In the example embodiment shown in FIG. 5A, network 80 comprises a 8×6 grid of markers 82 spaced an equidistance apart from one another.

However, network 80 may comprise any arrangement and configuration of markers 82 provided that the location of each marker is known.

Each marker 80 in the network of markers 82 has a distinct pattern. In some embodiments, each marker 80 may comprise a distinct black and white pattern.

Camera 70 may provide real-time images and/or a video stream of network 80 to an external computer system to estimate the position of UAV 10, 11. Provided camera 70 is able to image at least one marker 82, the position of UAV 10, 11 may be estimated. In some embodiments, UAV 10, 11 can detect and recognize at least four markers 82.

In some embodiments, UAV 10, 11 is configured to adjust a height (altitude) at which UAV 10, 11 is flying to maintain a certain number of markers 82 in view of camera 70. In some embodiments, UAV 10, 11 must be at least about 30 cm above network 80 to detect at least four markers 82.

In flight, UAV 10, 11 uses camera 70 to detect and identify markers 82 of network 80. In some embodiments, to detect and identify markers 82, camera 70 automatically extracts contour and/or filters acquired images. In other embodiments, contour extraction and filtering is performed by an external computer and image data is transmitted from camera 70 via WiFi, satellite, and/or mobile connection.

In some embodiments, each marker 82 comprises a unique ArUco code or QRCode as shown in FIG. 5B. An ArUco code or QRCode consists of black squares arranged in a square grid on a white background, a photograph of which can be captured by an imaging device (e.g. camera 70). The arrangement of black squares in the ArUco code or QRCode may then be extracted from the imaged marker to match the imaged marker with a marker in a database of known markers and marker locations. The matched marker may then be used to determine the position of UAV 10, 11 relative to the ArUco codes.

In some embodiments, a localization module may capture images of network 80, and detect contours from the images of network 80. Contours in the images indicate the presence of squares, and therefore markers 82, in the images. Images lacking contours may be rejected from further processing. The black and white squares in each image may then be identified by dividing the image into cells using horizontal and vertical grid lines. Depending on the amount of black or white pixels present in each grid region, each grid region is then assigned a value of 0 (white) or 1 (black) (or vice versa). The resulting pattern of black and white regions in each image is then compared to a database of black and white regions for known markers 82 in the network 80 of markers, and the image may be matched to a known marker. The position of UAV 10, 11 may then be determined from the position of the known marker. The position of UAV 10, 11 may be represented as a translation vector from the known marker, where the translation vector represents a direction and distance of UAV 10, 11 from the known marker.

In some embodiments, four markers 82 may be imaged, and the position of camera 70 may be taken as an average of the positions computed according to each detected marker 82.

In some embodiments, an adaptive threshold may be used to permit marker detection in poor light conditions. For example, if less than a threshold number of pixels in an image are designated as white pixels, then a threshold illumination level for identifying a pixel as white may be lowered. Similarly, if more than a threshold number of pixels in an image are designated as black pixels, then a threshold illumination level for identifying a pixel as black may be increased.

Figure 6A:
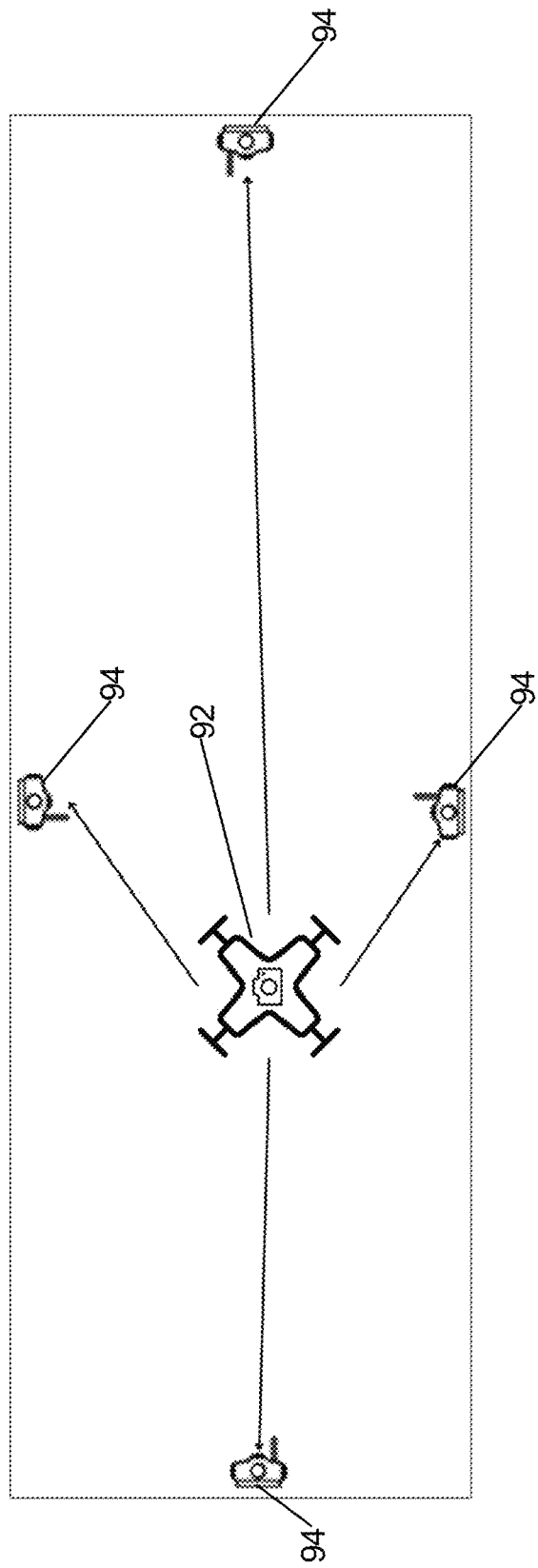
FIGS. 6A and 6B depict an indoor-GPS according to an example embodiment.
Figure 6B:
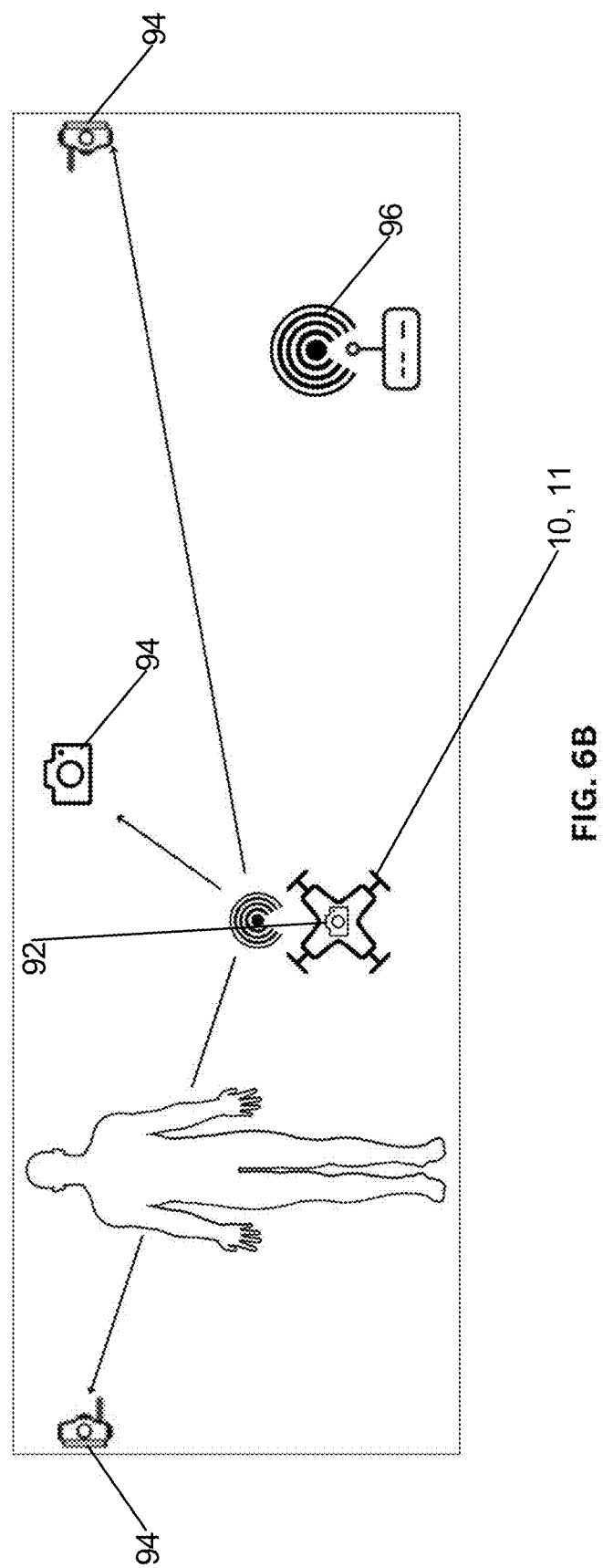

FIGS. 6A-6B illustrate an indoor-GPS 90 according to an example embodiment. Indoor-GPS 90 comprises a transmitter 92 mounted to UAV 10, 11, at least one receiver 94, and a modem 96. In the embodiments illustrated in FIGS. 3A-4D, transmitter 92 is mounted to a top surface 12*d* of body 12 to decrease propeller noise and/or increase the accuracy of navigation. Transmitter 92 may be mounted to alternative positions of body 12 provided UAV 10, 11 (and the parts thereof) do not obscure or weaken the strength of the signal emitted by transmitter 92 to a level which cannot be received by receivers 94.

In some embodiments, receivers 94 have an unobstructed line of sight to transmitter 92.

Transmitter 92 emits a signal periodically to provide geolocation and time information to receivers 94. In some embodiments, transmitter 92 emits a signal every 0.1 seconds to 5 seconds. In some embodiments, transmitter 92 emits a signal every 2 seconds.

A time between when transmitter 92 transmits a signal and when each of receivers 94 receive the signal is proportional to the distance from transmitter 92 to each of receivers 94. Such time delay between transmission of the signal and reception of the signal by each of receivers 94 may be used to determine the position of transmitter 92, and thereby the position of UAV 10, 11.

In some embodiments, receivers 94 determine a position of transmitter 92 by computing one or more navigation equations (e.g. a trilateration algorithm) to determine the position of transmitter 92. In some embodiments, indoor-GPS 90 comprises four receivers 94 configured to measure four time delays for a signal transmitted by transmitter 92. In some embodiments, the four time delays are used to compute a system of four equations, wherein the four equations represent three position coordinates and a clock deviation. The clock deviation may be used to correct for clock deviations between receivers 94.

In some embodiments, indoor-GPS 90 may be configured to autonomously determine a position of each of receivers 94 and determine a map of receivers 94. Indoor-GPS 90 may determine a location of receivers 94 by each of receivers 94 emitting a signal which is then received by each other of receivers 94. Indoor-GPS 90 may then determine a position of each of receivers 94 similar to determining the position of transmitter 92 described above. A map of receivers 94 may then be determined from the position of each of receivers 94. The map of receivers 94 may be stored in the memory of a modem 96.

Although the embodiment shown in FIG. 6A comprises four receivers 94, more or fewer receivers may be used. One or more receivers 94 may be mounted to one or more walls and/or the ceiling inside a confined space. For example, for the embodiment shown in FIG. 6A, a receiver 94 is mounted to each of the four walls of a rectangular room. The configuration of the walls may take on other geometric shapes (e.g. triangular, square, etc.).

In some embodiments, guidance system 130 uses a library such as the Open Computer Vision (OpenCV™) for human body skeleton detection and tracking. The input to guidance system 130 may be a video stream, for example a video stream from imaging system 110. The input video stream is processed frame by frame. A plurality of major body joints of a subject being imaged are identified and tracked by guidance system 130. A skeletal model is then generated from the identified major body joints. The skeletal model may then be used by guidance system 130 to control platform 120, for example to align platform 120 and imaging system 110 with an area of interest of a subject. The area of interest may then be imaged using imaging system 110. By generating the skeletal model, guidance system 130 may compensate for unintentional subject movement during an imaging session, and/or between imaging sessions.

In some embodiments, UAV 200, 10, 11 comprises one or more laser sensors to prevent collision of UAV 200, 10, 11 with other objects. The one or more laser sensors detect objects proximate the UAV 200, 10, 11. If an object is detected within an threshold distance of UAV 200, 10, 11, UAV 200, 10, 11 may autonomously navigate to avoid a collision with the detected object. In some embodiments, UAV 200, 10, 11 may stop or hold position when an object is detected within a threshold distance of UAV 200, 10, 11.

In some embodiments, UAV 200, 10, 11 comprises one or more laser sensors for determining the height of the UAV relative to the ground.

Analysis system 140 may comprise computer software to acquire, store, process, manage, and/or manipulate digital images. In some embodiments, the software may be stored on UAV 200, 10, 11, a mobile device carried by UAV 200, 10, 11, and/or a computer in communication with UAV 200, 10, 11, for example computer 220. The software may be used to improve image quality. For example, the software may be used to control illumination and/or colour, bring an object to be imaged into focus, and/or correct image defects (for example, by making corrections for artifacts such as oil or gel bubbles, hair, and/or shadows). The software may use a graphics processing unit and/or central processing unit to process images in real-time.

Where UAV 200, 10, 11 is used to digitally image skin, the software may be used to label, archive, monitor, and/or analyze skin features including, but not limited to, lesions, psoriasis, eczema, wounds, and wrinkles. For example, the software may be used to monitor changes in the height, diameter, and/or pigmentation of such skin features by comparing two or more digital images acquired at different times. In some embodiments, the appearance and/or disappearance of skin features may be monitored over subsequent images.

In some embodiments, the software is configured to process image data to calculate an ABCD (i.e. "Asymmetry, Border, Colors, and Dermoscopic structures") score and/or other conventional dermoscopic criteria. Such processing may be used to analyze skin lesions such as pigmented and non-pigmented lesions. For example, the automated analysis of the data captured may be used to determine if a lesion is prone to be benign or malignant growth and if further treatment and examination is recommended. The software may also recommend a personalized skin care and/or treatment plan. The software can also generate a report to be sent to a specialist for further examination and monitoring.

The software may provide a database of images for comparison and diagnostic purposes. Diagnosis may be performed automatically by the software and/or performed by a user or the user's physician.

Figure 6C:
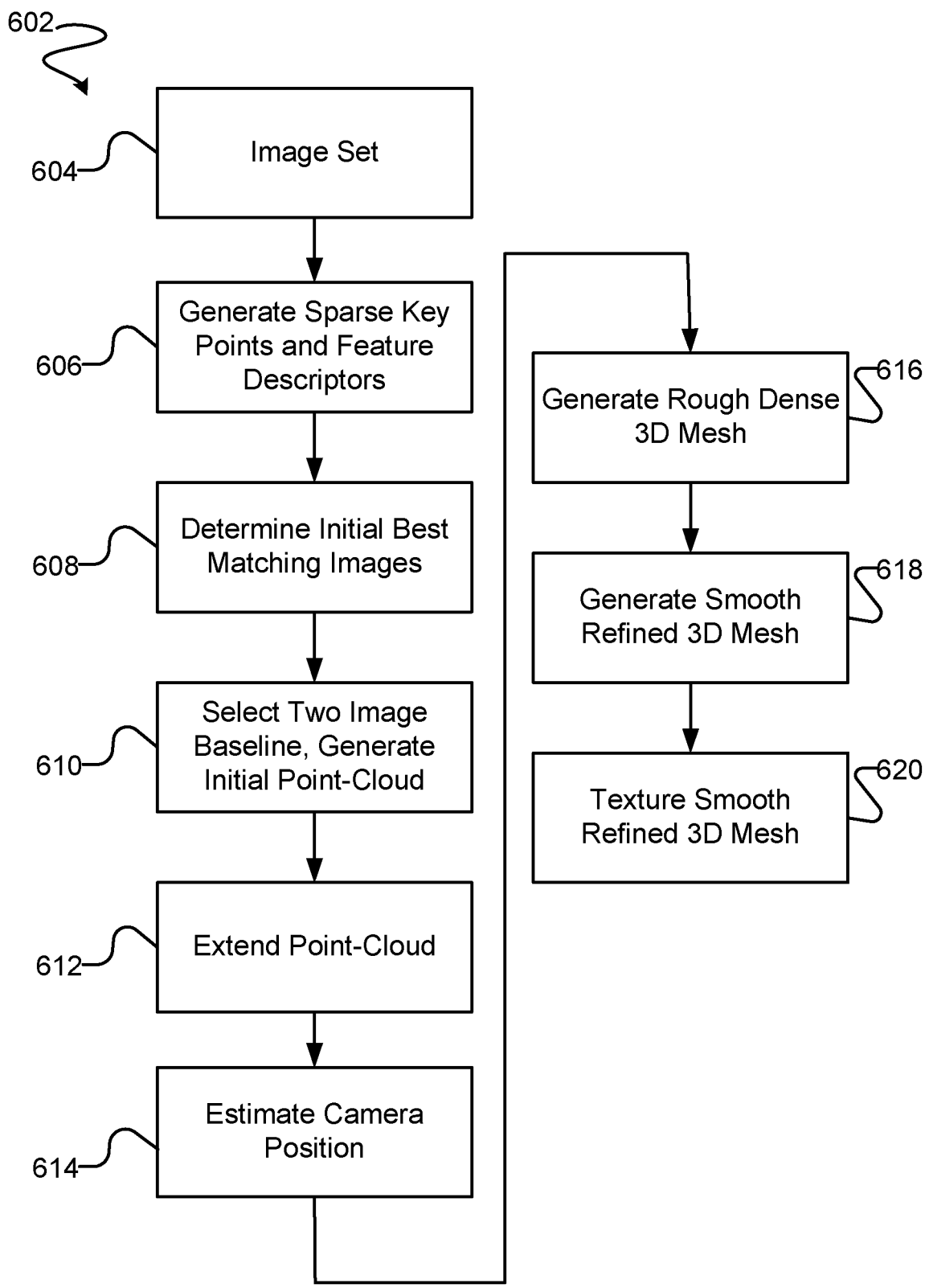
FIG. 6C depicts a 3D reconstruction method according to an example embodiment.

In some embodiments, UAV 200, 10, 11 may be configured to capture multiple images of an object from different viewpoints to construct a three-dimensional (3D) reconstruction of the object. FIG. 6C depicts an example embodiment of 3D reconstruction method 602.

The input of 3D reconstruction algorithm 602 is a set of images 604 captured from different angles with varying degree of overlap. In first step 606 of the 3D reconstruction algorithm, a set of sparse key points is generated for each image in the set of overlapping images, and a set of feature descriptors (compact numerical representations) is generated from the set of sparse key points.

In some embodiments, the sparse key points may comprise corner points determined using one or more methods described in U.S. Pat. No. 6,711,293 titled Method and apparatus for identifying scale invariant features in an image and use of same for locating an object in an image, or in *Fast explicit diffusion for accelerated features in nonlinear scale spaces* by Pablo F Alcantarilla, Jesús Nuevo, and Adrien Bartoli. (Trans. Pattern Anal. Machine Intell, 34(7):1281-1298, 2011), hereby incorporated by reference.

In second step 608 of the 3D reconstruction algorithm, photometric matches between each image are determined based on a number of feature descriptors in common between two images. An Euclidean distance from each feature descriptor to each other feature descriptor is determined, and the Euclidean distances are compared to determine an initial set of photometric matches comprising the best matching images.

In step 610, two images are selected from the initial set of best matching images as an initial baseline from which to construct an initial sparse 3D point-cloud. The two initial images may be selected based on a number of corresponding feature descriptors.

In step 612, the initial sparse 3D point-cloud is then iteratively extended by adding images from the set of images by using pose estimation and triangulation, for example using an incremental structure from motion (SfM) algorithm. Key point matches may be removed which have similar descriptors but are incorrect in their geometric location with respect to other key point matches.

Once the sparse 3D point-cloud is generated, the position of the camera in space may be estimated in step 614, for example by using a method described in *Adaptive structure from motion with a contrario model estimation* by Pierre Moulon, Pascal Monasse, and Renaud Marlet. (ACCV, 2012), hereby incorporated by reference herein.

From the sparse 3D point-cloud and position of the camera, a rough dense 3D mesh may be generated in step 616. A smooth refined 3D mesh may then be generated from the rough dense 3D mesh in step 618. Finally, the smooth refined 3D mesh is textured in step 620 using the initial set of imaged to generate a textured 3D model.

In some embodiments, the dense point-cloud may be generated according to a method described in *PatchMatch: A randomized correspondence algorithm for structural image editing* by Barnes, C., Shechtman, E., Finkelstein, A. and Goldman, D. B. (ACM Transactions on Graphics (ToG), 28(3), 2009), hereby incorporated by reference.

In some embodiments, the smooth refined 3D mesh may be generated according to a method described in *High accuracy and visibility-consistent dense multiview stereo* by Vu, H. H., Labatut, P., Pons, J. P. and Keriven, R. (IEEE transactions on pattern analysis and machine intelligence, 34(5)), hereby incorporated by reference.

In some embodiments, the UAV 200, 10, 11 may acquire an image of a skin lesion of a subject and map the lesion image to a previously identified skin lesion on a body map of the subject. UAV 200, 10, 11 may use automated or supervised pattern-matching to map the skin lesion in the image to a previously identified skin lesion. The image may be a lower quality overview image acquired using a digital camera, or higher quality dermoscopy image acquired using a dermoscope.

FIG. 7A is a schematic top view of an embodiment of system 100 comprising an unmanned ground vehicle (UGV)

700, and FIG. 7B is a schematic front view of UGV 700. UGV 700 comprises body 710. UGV 700 is propelled by two or more wheels 720. Wheels 720 are powered by one or more motors 730 mounted to body 710.

To navigate UGV 700 about a subject, UGV 700 further comprises a guidance system. The guidance system comprises an indoor global positioning system (indoor-GPS). The indoor-GPS may provide accurate location data for UGV 700, similar to the indoor-GPS system of UAV 10, 11 as described above.

UGV 700 further comprises digital camera 740, light source 750, sensors 760, and controller 770. Controller 770 is communicatively coupled to digital camera 740, light source 750, sensors 760, and motors 730.

FIG. 7 illustrates an embodiment of UGV 700 wherein sensor 760 comprises a camera 761 of the localization module. Camera 761 is positioned and oriented to acquire images of a network of markers positioned on the ground about an object.

Light source 750 is configured to illuminate a region proximate to UGV 700, and digital camera 740 is configured to capture images of subjects illuminated by light source 750.

In some embodiments, instead of digital camera 740, UGV 700 may comprise a mount configured to receive a computing device comprising an imaging system, for example a tablet computer comprising a camera such as an Apple iPad™'.

Figure 8:
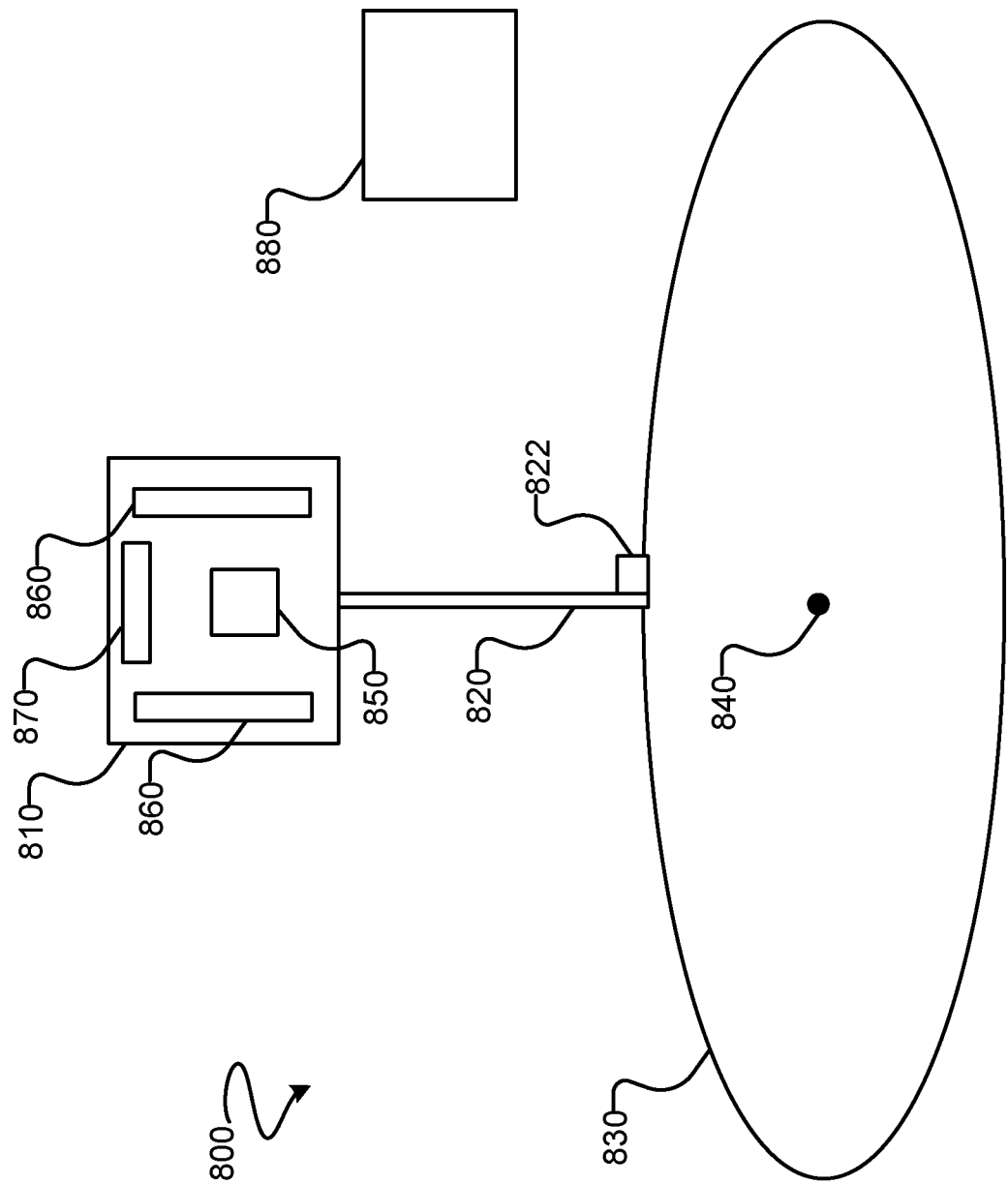
FIG. 8 depicts a circular stand according to an example embodiment.

FIG. 8 is a schematic view of an embodiment of system 100 comprising circular stand 800. Circular stand 800 comprises body 810 mounted on pedestal 820. Pedestal 820 is mounted to track 830. Track 830 follows a substantially circular path about center 840. Pedestal 820 comprises motor 822 for propelling pedestal 820 along track 830.

Digital camera 850, light source 860, and sensors 870 are mounted on body 810. Light source 860 is configured to illuminate a subject located at center 840, and digital camera 850 is configured to photograph a subject at center 840 illuminated by light source 860.

Circular stand 800 is communicatively coupled to control system 880. Control system 880 may be communicatively coupled by a wired and/or wireless connection to digital camera 850, light source 860, sensors 870, and motor 822. Control system 880 receives sensor data from sensors 870 and digital images from camera 850. Control system 880 may receive user input, and/or access stored digital images. Stored digital images may include digital images previously taken of a subject.

Control system 880 controls circular stand 800 based on one or more of: sensor data received form sensors 870, digital images received from digital camera 850, user input, and stored digital images.

Figure 9A:
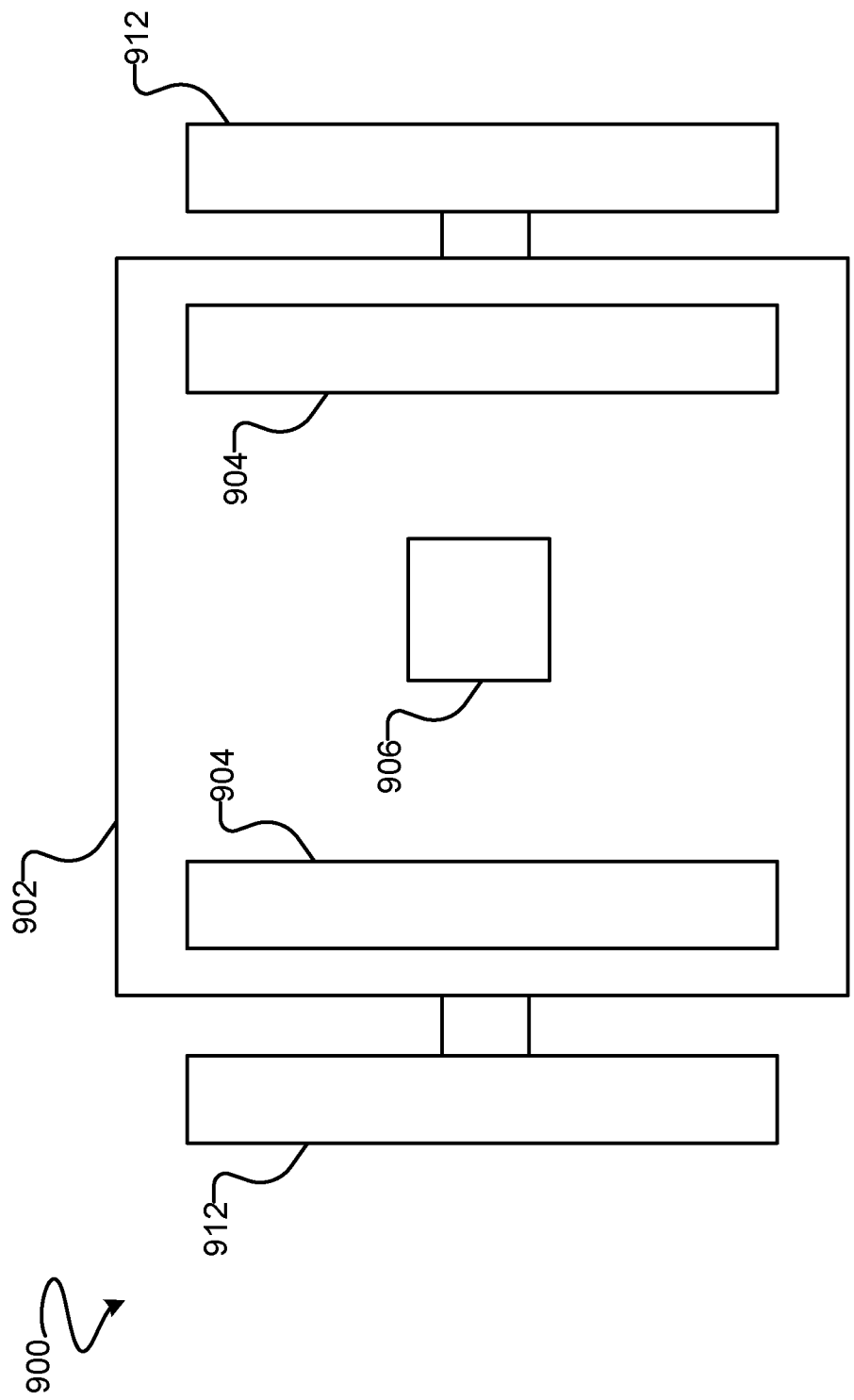
FIGS. 9A and 9B depict a flash light case according to an example embodiment.

FIG. 9A depicts a schematic view of an embodiment of imaging system comprising flash light case 900. A flash light case is hand-held device comprising one or more light sources and a mount for an imaging device. The light sources of the flash light case are configured to illuminate a region proximate the flash light case, and the mount of the flash light case is configured to orientate an imaging device towards the region illuminated by the light sources when an imaging device is mounted on the mount.

Flash light case 900 comprises body 902, light source 904 and mount 906. Light source 904 and mount 906 are attached to body 902. Mount 906 is configured to receive a computing device comprising an imaging system, for example a tablet computer comprising a camera such as an Apple iPad™'.

Flash light case 910 further comprises handles 912 attached to body 902. Handles 912 support body 902. Handles 912 are configured to be grasped by a user of flash light case 910.

Figure 9B:
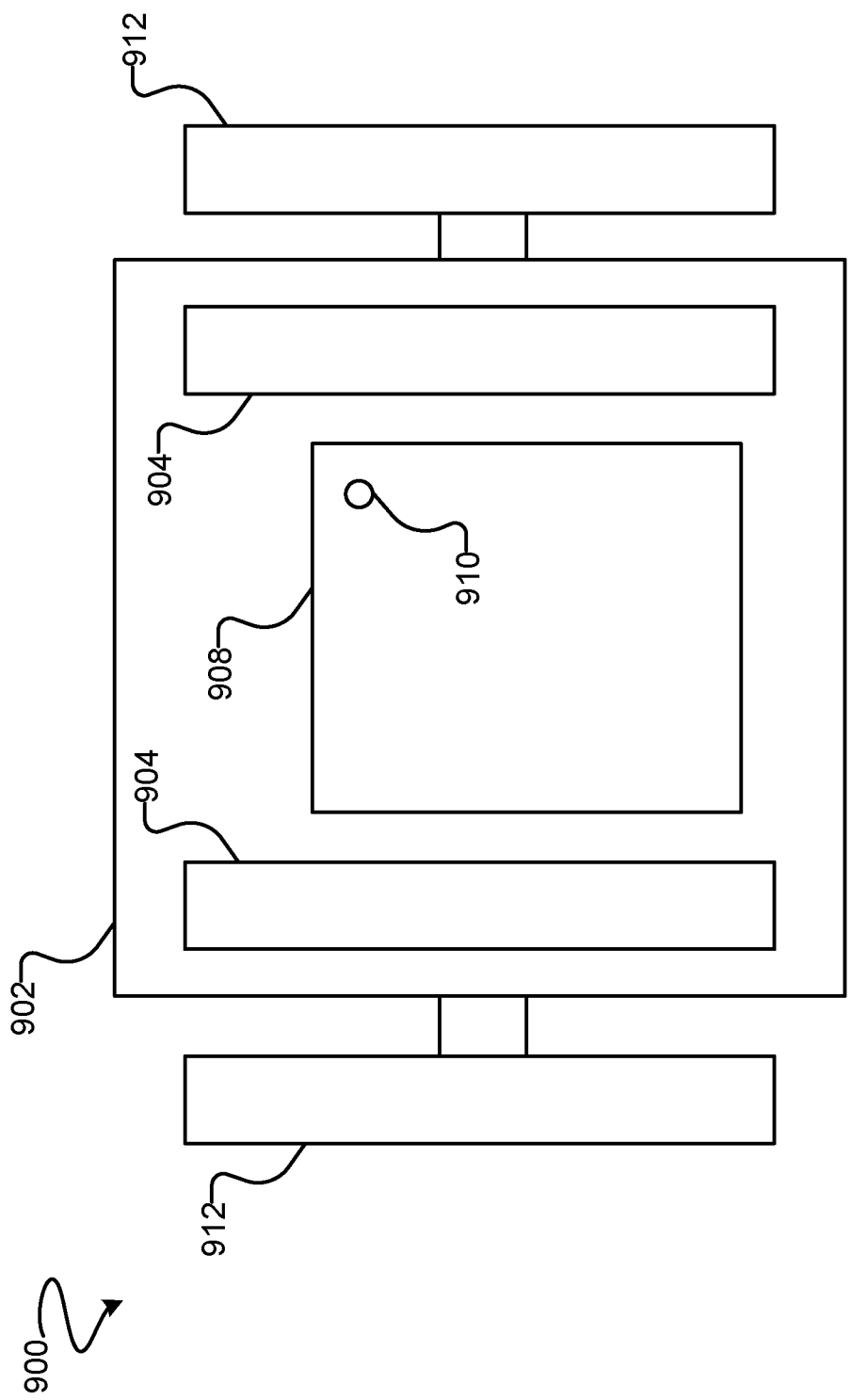

FIG. 9B depicts computing device 908 received by mount 904. Computing device 908 comprises digital camera 910. As depicted in FIG. 9B, when computing device 908 is received by mount 904, digital camera 910 is oriented towards a subject illuminated by light source 904. By grasping handles 912, a user may move flash light case 900 about a subject, and orientate light source 904 and a digital camera 910 relative to the subject.

Computing device 908 may be configured to provide commands to a user of flash light case 910 for moving flash light case 910 and controlling digital camera 910. For example, computing device 908 may generate a command to move flash light case 910 to orientate digital camera 910 relative to a feature of a subject, and photograph the feature with digital camera 910.

Interpretation of Terms

Unless the context clearly requires otherwise, throughout the description and the claims:

"comprise", "comprising", and the like are to be construed in an inclusive sense, as opposed to an exclusive or exhaustive sense; that is to say, in the sense of "including, but not limited to";

"connected", "coupled", or any variant thereof, means any connection or coupling, either direct or indirect, between two or more elements; the coupling or connection between the elements can be physical, logical, or a combination thereof; elements which are integrally formed may be considered to be connected or coupled;

"herein", "above", "below", and words of similar import, when used to describe this specification, shall refer to this specification as a whole, and not to any particular portions of this specification;

"or", in reference to a list of two or more items, covers all of the following interpretations of the word: any of the items in the list, all of the items in the list, and any combination of the items in the list;

the singular forms "a", "an", and "the" also include the meaning of any appropriate plural forms.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Software and other modules may reside on servers, workstations, personal computers, tablet computers, image data encoders, image data decoders, PDAs, color-grading tools, video projectors, audio-visual receivers, displays (such as televisions), digital cinema projectors, media players, and other devices suitable for the purposes described herein. Those skilled in the relevant art will appreciate that aspects of the system can be practised with other communications, data processing, or computer system configurations, including: Internet appliances, hand-held devices (including personal digital assistants (PDAs)), wearable computers, all manner of cellular or mobile phones, multi-processor systems, microprocessor-based or programmable consumer electronics (e.g., video projectors, audio-visual receivers, displays, such as televisions, and the like), set-top boxes, color-grading tools, network PCs, mini-computers, mainframe computers, and the like.

The invention may also be provided in the form of a program product. The program product may comprise any non-transitory medium which carries a set of computer-readable instructions which, when executed by a data processor, cause the data processor to execute a method of the invention. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or preprogrammed chips (e.g., EEPROM semiconductor chips), nanotechnology memory, or the like. The computer-readable signals on the program product may optionally be compressed or encrypted.

In some embodiments, the invention may be implemented in software. For greater clarity, "software" includes any instructions executed on a processor, and may include (but is not limited to) firmware, resident software, microcode, and the like. Both processing hardware and software may be centralized or distributed (or a combination thereof), in whole or in part, as known to those skilled in the art. For example, software and other modules may be accessible via local memory, via a network, via a browser or other application in a distributed computing context, or via other means suitable for the purposes described above.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

While a number of exemplary aspects and embodiments are discussed herein, those of skill in the art will recognize certain modifications, permutations, additions and sub-combinations thereof.

Various features are described herein as being present in "some embodiments". Such features are not mandatory and may not be present in all embodiments. Embodiments of the invention may include zero, any one or any combination of two or more of such features. This is limited only to the extent that certain ones of such features are incompatible with other ones of such features in the sense that it would be impossible for a person of ordinary skill in the art to construct a practical embodiment that combines such incompatible features. Consequently, the description that "some embodiments" possess feature A and "some embodiments" possess feature B should be interpreted as an express indication that the inventors also contemplate embodiments which combine features A and B (unless the description states otherwise or features A and B are fundamentally incompatible).

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

The invention claimed is:

1. A method of photographing at least a portion of a person with a platform carrying an imaging system, the method comprising:
   generating a photography scheme, the photography scheme comprising a set of photography control points, each of the photography control points comprising:
      a location of the platform relative to a representative person;
      an orientation of the platform relative to the representative person; and
      one or more photography parameters;
   instructing the person to assume a position and an orientation of the representative person;
   determining a position and an orientation of the person, wherein determining the position and the orientation of the person comprises retrieving the position and the orientation of the representative person;
   determining a location and an orientation of the platform carrying the imaging system;
   navigating the platform to each of the photography control points and operating the imaging system to capture an image of the person at each of the photography control points according to the associated photography parameters.

2. The method according to claim 1, wherein generating the photography scheme comprises:
   determining a distance between the representative person and the platform for each of the photography control points; and
   determining an orientation of the platform relative to the representative person for each of the photography control points.

3. The method according to claim 1, comprising:
   receiving a previously captured image of the person;
   determining one or more photography parameters associated with the previously captured image; and
   wherein generating the photography scheme comprises generating one or more photography control points with photography parameters equal to the photography parameters associated with the previously captured image.

4. The method according to claim 3, comprising:
   determining a location and an orientation of the platform relative to the person associated with the previously captured image; and
   wherein generating the photography scheme comprises generating a photography control point with:
      a location of the platform relative to the person equal to the location of the platform relative to the person associated with the previously captured image; and an orientation of the platform relative to the person equal to the orientation of the platform relative to the person associated with the previously captured image.

5. The method according to claim 1, wherein navigating the platform to each of the photography control points comprises:
determining a current position of the platform;
determining a translation vector representing a direction and distance from the current position of the platform to one of the photography control points; and
navigating the platform for the distance and in the direction of the translation vector.

6. The method according to claim 1, wherein determining the location of the platform comprises:
capturing an image of a marker;
matching the image of the marker to a known marker in a set of known markers, wherein each of the known markers is associated with a corresponding marker location; and
determining the position of the platform from the known marker and corresponding marker location.

7. The method according to claim 6, wherein each of the known markers is associated with a corresponding marker orientation, and determining the orientation of the platform comprises:
determining an orientation of the marker in the image of the marker; and
determining the orientation of the platform from the orientation of the marker in the image of the marker and the corresponding marker orientation of the known marker.

8. The method according to claim 1, wherein determining the location and the orientation of the platform comprises:
transmitting a signal from the platform;
receiving the signal with three receivers with known locations;
determining time delays of the signal to the three receivers; and
determining a position of the platform from the time delays and known locations of the receivers.

9. The method according to claim 1, wherein:
a smartphone comprising a digital camera is mounted to the platform; and
the imaging system comprises the digital camera of the smartphone.

10. The method according to claim 1, wherein:
the platform comprises a propulsion system; and
the platform is at least partially self-propelled by the propulsion system.

11. The method according to claim 10, wherein:
a smartphone comprising a digital camera is mounted to the platform;
the imaging system comprises the digital camera of the smartphone;
the smartphone is communicatively coupled to the platform to control the propulsion system; and
navigating the platform to each of the photography control points comprises the smartphone controlling the propulsion system to navigate the platform to each of the photography control points.

12. The method according to claim 11, wherein the smartphone comprises a memory and the photography scheme is stored in the memory of the smartphone.

13. The method according to claim 12, wherein navigating the platform to each of the photography control points comprises executing guidance software with the smartphone stored in the memory of the smartphone.

14. The method according to claim 1, wherein:
the platform comprises an aerial drone;
the imaging system comprises a digital camera mounted to the aerial drone; and
navigating the platform to each of the photography control points comprises flying the aerial drone to each of the photography control points.

15. The method according to claim 1, wherein:
the platform comprises an unmanned ground vehicle (UGV);
the imaging system comprises a digital camera mounted to the UGV; and
navigating the platform to each of the photography control points comprises driving the UGV between each of the photography points.

* * * * *